(12) United States Patent
Chadwick et al.

(10) Patent No.: US 12,394,408 B1
(45) Date of Patent: Aug. 19, 2025

(54) VOICE ANALYZER FOR INTERACTIVE CARE SYSTEM

(71) Applicant: Live Circle Inc., Ridgewood, NJ (US)

(72) Inventors: Charles Chadwick, Ridgewood, NJ (US); Samuel Brotherton, Park City, UT (US)

(73) Assignee: LIVE CIRCLE, INC., Ridgewood, NJ (US)

( * ) Notice: Subject to any disclaimer, the term of this patent is extended or adjusted under 35 U.S.C. 154(b) by 40 days.

(21) Appl. No.: 17/074,270

(22) Filed: Oct. 19, 2020

Related U.S. Application Data

(60) Provisional application No. 62/916,793, filed on Oct. 17, 2019.

(51) Int. Cl.
| | |
|---|---|
| *G10L 15/10* | (2006.01) |
| *A61B 5/00* | (2006.01) |
| *A61B 5/16* | (2006.01) |
| *G06F 16/65* | (2019.01) |
| *G10L 15/06* | (2013.01) |
| *G10L 15/183* | (2013.01) |
| *G16H 50/20* | (2018.01) |

(52) U.S. Cl.
CPC .............. *G10L 15/10* (2013.01); *A61B 5/165* (2013.01); *A61B 5/4803* (2013.01); *A61B 5/7267* (2013.01); *A61B 5/7282* (2013.01); *A61B 5/742* (2013.01); *G06F 16/65* (2019.01); *G10L 15/063* (2013.01); *G10L 15/183* (2013.01); *G16H 50/20* (2018.01)

(58) Field of Classification Search
CPC ..... G10L 15/10; G10L 15/063; G10L 15/183; G06F 16/65; A61B 5/165; A61B 5/4803; A61B 5/7267; A61B 5/7282; A61B 5/742; G16H 15/20
See application file for complete search history.

(56) References Cited

U.S. PATENT DOCUMENTS

| | | | |
|---|---|---|---|
| 10,796,714 B2 | 10/2020 | Levanon et al. | |
| 11,120,895 B2 | 9/2021 | Shriberg et al. | |
| 11,301,758 B2 | 4/2022 | De et al. | |
| 2007/0214011 A1* | 9/2007 | Demers | G16H 80/00 600/300 |
| 2016/0308799 A1* | 10/2016 | Schubert | H04L 67/535 |
| 2018/0254041 A1* | 9/2018 | Harper | G10L 25/51 |
| 2018/0336413 A1* | 11/2018 | Zhao | G06Q 50/265 |
| 2019/0011461 A1* | 1/2019 | Wallach | A61K 31/53 |
| 2019/0237201 A1* | 8/2019 | Bauman | G16H 50/30 |
| 2020/0105274 A1* | 4/2020 | Joller | G06F 16/635 |
| 2020/0152304 A1 | 5/2020 | Chang et al. | |

(Continued)

OTHER PUBLICATIONS

Wang, Daisy Zhe, "A Probabilistic Knowledge Base System", (PowerPoint presentation). Data Science Research CISE University of Florida, 2013.

(Continued)

*Primary Examiner* — Daniel C Washburn
*Assistant Examiner* — Paul J. Mueller

(57) ABSTRACT

A support interaction is guided in real time by generating from audio content featurized audio data that includes audio segments and audio features; generating in real time classification scores associated with certain audio segments; and displaying in real time the classifications scores and information associated with the corresponding audio segments.

52 Claims, 15 Drawing Sheets

(56) References Cited

U.S. PATENT DOCUMENTS

| | | | |
|---|---|---|---|
| 2020/0175987 A1* | 6/2020 | Thomson | G10L 15/26 |
| 2021/0035575 A1* | 2/2021 | An | G06F 3/167 |
| 2021/0082563 A1* | 3/2021 | Wingfield | G16H 10/60 |
| 2022/0068482 A1* | 3/2022 | Zimmerman | G16H 70/20 |

OTHER PUBLICATIONS

Demiris, George, et al., "Spoken words as biomarkers: using machine learning to gain insight into communication as a predictor of anxiety", Journal of the American Medical Informatics Association, 27(6), May 6, 2020, 929-933.

Chadwick, Charles, "Live Circle Family Caregiver Conversations", (Confidential PowerPoint presentation), Feb. 22, 2019. Comcast Center, 1701 John F Kennedy Blvd., Philadelphia, PA 19103—Redacted.

Narayanan S., et al., "Behavioral Signal Processing: Deriving Human Behavioral Informatics From Speech and Language", Proc. IEEE PP (99) (2013) 1-31.

Baucom, B., et al. "The Promise and the Challenge of Technology-Facilitated Methods for Assessing Behavioral and Cognitive Markers of Risk for Suicide among U.S. Army National Guard Personnel", Int. J. Environ. Res. Public Health 14 (4) (2017) 361.

Chuang, Z., et al., "Emotion recognition via acoustic features and semantic contents in speech", International Symposium on Chinese Spoken Language Processing (ISCSLP) 2002, vol. 1, pp. 53-56.

Alam, F., et al., "Can we detect speakers' empathy? A real-life case study", 2016 7th IEEE International Conference on Cognitive Infocommunications (CogInfoCom), 2016, pp. 000059-000064.

Zvarevashe, K., et al., Ensemble Learning of Hybrid Acoustic Features for Speech Emotion Recognition, Algorithms 13 (3) (2020) 70.

Reinhard, S.C., et al., "Valuing the Invaluable: 2015 Undeniable progress, but big gaps remain", AARP Public Policy Institute Insight on the Issues (Washington, DC: AARP, Jul. 2015).

Brodaty, H., et al., "Who cares for the carer? The often forgotten patient." Australian family physician 31, No. 9 (2002).

Schulz, R., et al., "Physical and mental health effects of family caregiving", Am. J. Nurs. 108 (Suppl 9) (2008) 23-27.

Aggar, C., et al., "Reactions to caregiving during an intervention targeting frailty in community living older people", BMC Geriatrics. 12 (2012) 66.

Schulz, R., et al., "Caregiving as a risk factor for mortality: The caregiver health effects study", JAMA 282 (23) (1999) 2215-2219.

Demiris, G., et al., "A problem-solving intervention for hospice family caregivers: A randomized clinical trial", Jrl. Amer. Geriat. Soc. 67 (7) (2019) 1345-1352.

Mcmillan, S.C., et al., "The impact of hospice services on the quality of life of primary caregivers," Oncol. Nurs. Forum 21 (7) (1994) 1189-1195.

Spitzer, R.L., et al., "A brief measure for assessing generalized anxiety disorder: the GAD-7", Arch. Intern. Med. 166 (10) (2006) 1092-1097.

Andreakou, A.A., et al. "Assessment of health-related quality of life for caregivers of Alzheimer's disease patients", Int. Jrl. Alzheimer's Disease 2016 (2016) 1-7.

Cuthbert, C.A., et al., "Exploring correlates of quality of life in older family caregivers to cancer patients", Jrl. Clin. Oncol. 34, 3 (suppl) (2016) Abstract #186.

Kim, Y., et al., "Quality of life of couples dealing with cancer: dyadic and individual adjustment among breast and prostate cancer survivors and their spousal caregivers", Ann. Behav. Med. 35 (2) (2008) 230-238.

Northouse, L.L., et al., "Couples' patterns of adjustment to colon cancer", Soc. Sci. Med. 50 (2) (2000) 271-284.

Andrieu, S., et al., "New assessment of dependency in demented patients: Impact on the quality of life in informal caregivers", Psychiatry Clin. Neurosci. 61 (3) (2007) 234-242.

Tooth, L., et al., "Impact of cognitive and physical impairment on carer burden and quality of life", Qual. Life Res. 17 (2008) 267-273.

Munikar, M., et al., "Fine-grained Sentiment Classification using BERT", Artificial Intell. Transforming Bus. Soc. (AITB) 2019 (2019) 1-5.

\* cited by examiner

VOICE ANALYZER FOR INTERACTIVE CARE SYSTEM

CROSS-REFERENCE TO RELATED APPLICATIONS

This application claims priority to and the benefit of U.S. provisional application Ser. No. 62/916,793 filed on Oct. 17, 2019 and entitled Artificial Intelligence System and Method for Use, which is commonly assigned and the contents of which are expressly incorporated herein by reference. This application is related to the copending U.S. patent application Ser. No. 17/074,617, by Charles Chadwick and Samuel Brotherton entitled Automated Predictive Care System filed on Oct. 19, 2020, the contents of which are expressly incorporated herein by reference, and is also related to the copending U.S. patent application Ser. No. 17/074,567, by Charles Chadwick and Samuel Brotherton entitled Method for Collaborative Knowledge Base Development filed on Oct. 19, 2020, the contents of which are expressly incorporated herein by reference.

STATEMENT REGARDING PRIOR DISCLOSURES BY THE INVENTOR OR A JOINT INVENTOR

Chadwick, Charles, "Live Circle Family Caregiver Conversations", (Confidential PowerPoint presentation), 22 Feb. 2019. Comcast Center, 1701 John F Kennedy Blvd., Philadelphia, PA 19103.

Demiris, George et. al, "Spoken words as biomarkers: using machine learning to gain insight into communication as a predictor of anxiety", Journal of the American Medical Informatics Association, 27 (6), 6 May 2020, 929-933.

FIELD OF THE INVENTION

The present invention relates to artificial intelligence-based language analysis methods and systems.

BACKGROUND

In the past, known artificial intelligence computational tools involving probabilistic programming have been used to create digital knowledge bases based on language analysis. Such knowledge bases are a collection of data representing entities, facts, and relationships that conform to a predefined data model. Such knowledge bases help machines to understand humans, language, and the world. See Wang, Daisy Zhe, "A Probabilistic Knowledge Base System", (PowerPoint presentation). Data Science Research CISE University of Florida, 2013, the contents of which are incorporated herein by reference in their entirety.

SUMMARY OF THE INVENTION

According to an aspect of the invention, a method for guiding a support interaction in real time, includes the steps of receiving a first audio content; generating from the first audio content featurized audio data comprising a plurality of audio segments and a plurality of audio features using at least one language featurization system trained on a first reference speech data; generating from the featurized audio data a plurality of classification scores associated with certain ones of the plurality of audio segments; associating the plurality of classification scores with respective ones of the plurality of audio segments; displaying, in real time, at least one of the plurality of classification scores and an information associated with the respective plurality of audio segments; updating a user database comprising user predicates using at least one of the plurality of audio segments; identifying at least one initial topic of interest based upon at least one of the plurality of audio segments, the user database, and a global database comprising use case predicates; converting the initial topic of interest to a natural language support interaction guidance and displaying the natural language support interaction guidance to an interviewer in real time; identifying at least one topic of greatest significance based upon the at least one initial topic of interest, the user database, and the global database; identifying a highest correlated action step based upon the topic of greatest significance; and communicating the highest correlated action step to a user.

According to a second aspect of the invention, a method for guiding a support interaction in real time, includes the steps of receiving a first audio content; generating from the first audio content featurized audio data comprising a plurality of audio segments and a plurality of audio features using at least one language featurization system trained on a first reference speech data; generating in real time from the featurized audio data a plurality of classification scores associated with certain ones of the plurality of audio segments, at least one of the plurality of classification scores usable in the assessment of a General Anxiety Disorder score; and displaying in real time at least one of the plurality of classification scores and an information associated with the respective plurality of audio segments.

According to a third aspect of the invention, a method for identifying and implementing a next action step includes the steps of receiving a first audio content; generating from the first audio content featurized audio data comprising a plurality of audio segments and a plurality of audio features using at least one language featurization neural network trained on a first reference speech data; generating from the featurized audio data a plurality of classification scores associated with certain ones of the plurality of audio segments; associating the plurality of classifications scores with respective ones of the plurality of audio segments; updating a user database comprising user predicates, using at least one of the plurality of audio segments; identifying at least one initial topic of interest based upon at least one of the plurality of audio segments, the user database, and a global database comprising use case predicates; identifying at least one topic of greatest significance based upon the at least one initial topic of interest, the user database, and the global database; identifying a highest correlated action step based upon the topic of greatest significance; identifying a plurality of resources necessary to accomplish the highest correlated action step; identifying at least one individual stakeholder associated with the highest correlated action step; and initiating contact with the plurality of resources and the at least one individual stakeholder during the step of receiving the first audio content.

BRIEF DESCRIPTION OF DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

Figure 1:
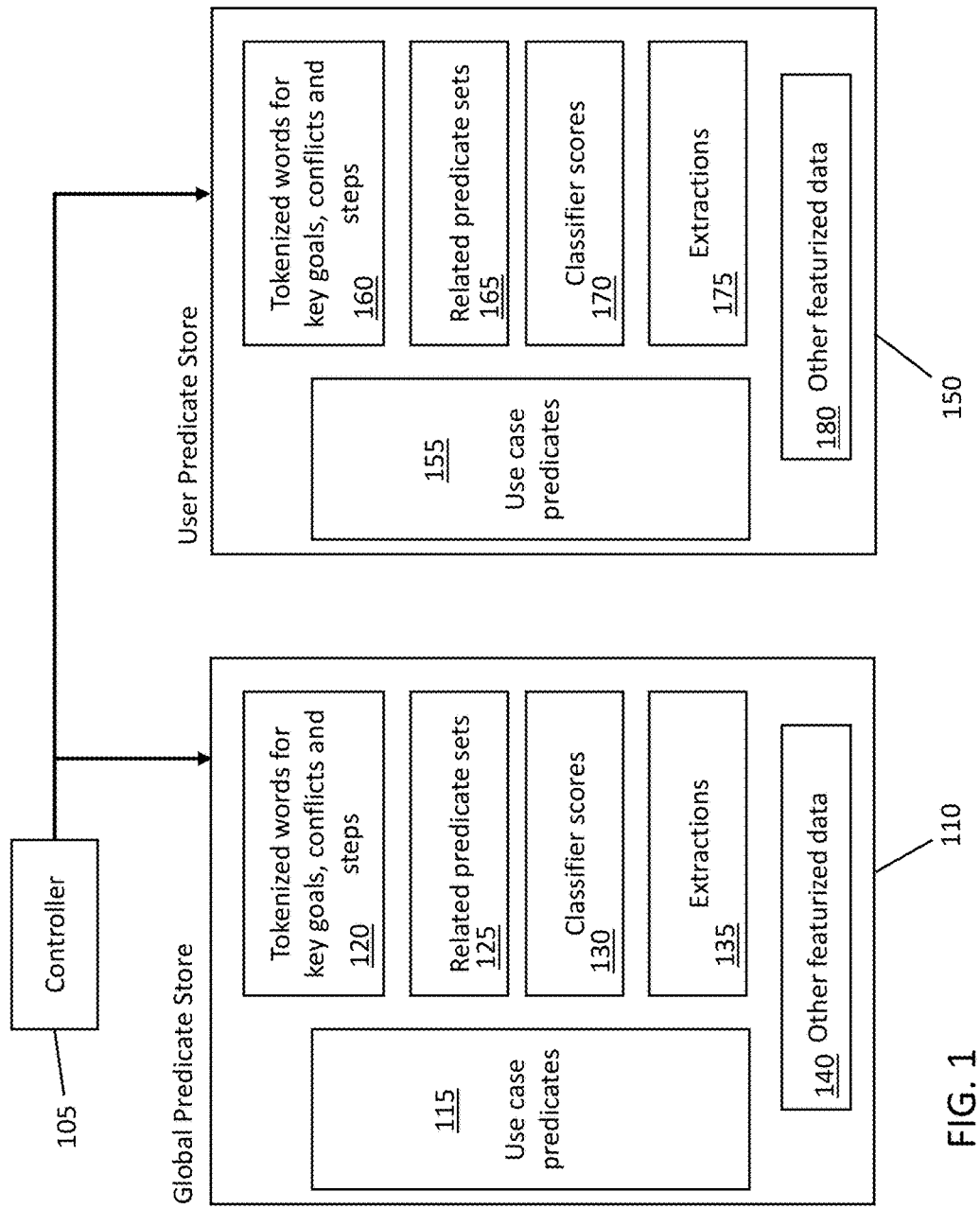
FIG. 1 is a block diagram of a use case database and a user database in accordance with various embodiments of the present invention.

So that the manner in which the features and advantages of embodiments of methods and systems of the present invention may be understood in more detail, a more particular description of the present invention briefly summarized above may be had by reference to certain embodiments thereof that are illustrated in the appended drawings, which form a part of this specification. The drawings illustrate only certain embodiments of the present invention and are, therefore, not to be considered limiting of the scope of the present invention which includes other useful and effective embodiments as well. For ease of description and understanding, the following embodiments are discussed mainly in connection with industrial system control applications but can be advantageously implemented in medical applications, financial systems, other algorithmically optimized control systems, and the like.

The present invention provides artificial intelligence (AI) language analysis systems and methods usable in a system for guiding live interactions between participants in a use case, and to identify and initiate action steps predicted to advance each participant towards a goal associated with that participant's context and circumstance in the given use case. Preferred embodiments of the present invention use AI computational tools involving probabilistic programming and neural networks to create and manage predicates representing the likely state of each user's use case, status, and situational context at any queried moment. The neural networks, which are trained to recognize, label and extract probabilistic predicates from user input based on a use case, are updated, managed, analyzed, and correlated with one another to accomplish the user's objectives. In preferred embodiments, the inventive method can be viewed as a probabilistic machine-learning-based expert system that connects the predicates for each user required by a given use case (and stored in individual user knowledge bases) and the predicates required for interactions between users or groups of users in a given use case (and stored in a probabilistic global knowledgebase for the given use case).

The methods of the present invention have applications in many contexts in additions to the preferred embodiments described here. This disclosure focuses on several preferred applications which are intended to be illustrative, and not limiting. Language, spoken and written, can be analyzed, and broken down into elements permitting artificial intelligence (AI) computational tools, in some cases employing probabilistic programming, and novel improvements to those tools, to predict the likely status and situational context of individuals and things. The probabilistic programming generates probabilities that a given fact is true, and can generate new facts from inference from other available facts, rather than following strict axioms or rules of traditional expert systems that rely on only true or false logical conditions. Instead, the invented system relies on neural networks trained on data and logical relationships between facts to assign a weight to initial facts, including those associated with initial user status and situational context. The system uses new facts, obtained from user input or input about the user, to update the probabilities.

A preferred embodiment of the system is implemented using a probabilistic programming language and platform that uses predicates in its logical reasoning functions such as, for example, ProbLog, well known to those skilled in the relevant art. For example, in Problog, the representation "1.0::is_named(User123, "Tom Garvin")" could be read as "We are 100% sure that User123's name is Tom Garvin", and "0.7::took_medication_on_day(User123, "statin", Mar. 10, 2018)" could be read as "We are 70% sure that Tom Garvin took his statins on Mar. 10, 2018.

The use of probability does not preclude certainty—for example, that User123 is "Tom Garvin." However, in the real world facts "change." While it may be true that a weekly work schedule exists, it may also be that half the time a weekly work schedule changes and that on some days it is more likely to change than on others. These facts enter the system through various means and are considered "facts," even if only they are actually probabilities of a statement being true.

For example, the invented system can determine the likelihood of a certain state of mind (or health condition) using neural networks trained on studied states of mind and data used to train the neural network on these states. Similarly, for an entity such as a pharmacy, its hours of service and medications in stock can be determined and characterized on the basis of probability.

AI computational tools examine the language elements to recognize and extract facts, things that can be known about a thing, as "probabilistic predicates." A "predicate" (also known as a "label") comprises a predicate head and a predicate argument (also known as the "predicate body"). For example, if the thing is a banana, a characteristic that can be known about it is its color. And that color, in the case of a banana, is yellow. For an individual, one thing that can be known is age, for example, 55 years. For the purposes of AI computational tools, a statement of the topic of interest, for example color or age, is referred to as the "predicate head." And the answer, yellow or 55, respectively, is referred to as the "predicate argument." Note that the arguments are susceptible to change and to being updated over time. Yellow at a later date might be brown. Age at a later date will be 56 years.

Also, language can be broken down and analyzed to characterize a set of circumstances that involve goals to be attained, and steps to accomplish to advance towards attaining those goals. For example, the circumstance of effectively managing the care of an elderly parent, while progressing through the logistics of health insurance claims associated with providing that care, can be characterized. Such sets of circumstances can be referred to as "use cases." Use cases may comprise any human interaction, the path towards achieving a goal, the solution to a problem, an application of technology, or the like.

The characterization of an individual's situational context can be tracked as it develops over time and that evolving characterization can be correlated to the characterization of a use case. The correlation can be used to determine where in the use case process the individual (or "subject") is, and what action steps will be helpful to advance the subject towards the goals defined for the use case.

Specifically, AI computational tools using probabilistic programming can construct a "knowledge graph" based on language-based characterizations reflecting a subject's likely location, or state, in the process of (or path along) the use case. In the healthcare example, the subject may have submitted claims forms and is likely to be awaiting a reimbursement check; and at the same time, the subject may have attempted to negotiate with her employer to change her work schedule so that she can care for her elderly parent on Sundays. In addition, the "knowledge graph" reflects actions steps contextually adjacent or near where the subject is likely to be in the use case process (or path), that can advance the subject towards the use case goals. For example, a potential next step may be interviewing for a new job that has weekends off which would allow the subject to care for her parent on Sundays.

There are numerous specific elements of language, spoken and written that, when operated on collectively, allow AI computational tools to accomplish the foregoing. These include, for spoken language, qualities of the associated audio signal such as loudness, loudness range, power, peak-to-average power ratio, and pitch characteristics including centroid, crest, flatness, kurtosis, roll-off, skewness, slope and spread. The language actually spoken can be converted into text and analyzed.

For written language, and text generated from voice-to-text conversion, a large number of language elements are available to analyze. They include individual words, referred to as tokens, combinations of words that ordinarily go together are referred to as ngrams (e.g., "heart attack," n being 2 in this example), and word "vectors," which may represent a token or ngram together with its potential substitutes, such as synonyms. When analysis is performed on spoken and written language to identify the foregoing language elements, the elements may be referred to as "features," and the automated development of language features may be referred to as "featurization."

In addition, there are ways to arrange words obtained from language analysis that facilitate the operation of the AI computational tools. Specifically, tokens, ngrams and vectors can be used to determine subject-verb-object sets. Subject-verb-object sets (SVOs) are natural language grammatical and semantic units. SVOs may be used to train the system of the present invention on use case elements described in natural language by use case developers and other participants who use the system. SVOs are easily converted into predicates using tokenization and other processes known in the art and can be used by AI tools to develop characterizations.

For non-language data, a conversion into language elements, or predicates, is performed that facilitates the use of the AI computational tools in clinical and other situations requiring precision. These conversions may involve supplied health status measurements, such as blood pressure readings or pulse rates or blood test results, which may provide a higher degree of probability of being true than language only representations. Compare "my heart is racing," expressed as a predicate, "0.85::is_state("heart","racing"), and a pulse rate of 140, expressed as predicate from the machine input, 1.0::is_measurement("pulse",140). In this manner, data and language elements can both be managed as predicates in the same system.

In one preferred application of the invention, a use case is defined in which a subject must traverse multiple challenges to attain a goal. The earlier provided example is an individual whose goal is to effectively manage the care of an elderly parent while progressing through the logistics of health insurance claims associated with providing that care. The use case may be characterized by AI computational tools operating on the subject's language, to produce a graph representing the subject's current status and the subject's predicted trajectory. Available actions steps can be developed and tracked.

In addition, the status and situational context of the subject (user) may be characterized, also by way of AI computational tools operating on the subject's language. In a number of preferred embodiments, the expressed language is obtained at least in part from live discussions between the subject and another party, who may be referred to as an "interviewer." For example, the language exchanged in a phone call between the subject and a nurse (the interviewer) whom the subject has been referred to by the insurance company may be analyzed.

The status and situational context of the subject includes determinations of probable, if not certain, facts, for example, the subject's age and work schedule. In a number of preferred embodiments, assessments of the subject's emotional state of mind may be estimated or otherwise determined, e.g.

scored. Preferably, AI computational tools are used to assess a subject's level of anxiety and comfort level with current quality of life (QoL). The anxiety level and QoL level may be scored with reference to clinically recognized validated health assessments, including GAD-7 and QoL clinical assessment protocols, respectively, and other conventional health assessments.

Typically, a reduced anxiety level and an improved QoL outlook are valuable goals in and of themselves in most cases. There will often be a correlation between reduced anxiety levels and improved QoL outlook, and accomplishing the practical goals associated with a use case. In the instant example, a revised schedule that makes the subject's weekends available for caring for the parent, and receiving the insurance claim reimbursement, may be expected to naturally reduce anxiety level and improve QoL outlook.

In certain preferred embodiments, state of mind scores for a subject, a subset of the general category of "health assessments," may drive the overall process for assisting the subject to traverse the use case. For example, an initial health assessment determined by AI language analysis (as will be more fully described), e.g., initial GAD and/or QoL score or the like, may set the starting point of a use case. A desired health assessment score may be established as a defined goal for the use case, among other potential goals.

A use case may include goals as well as relevant subgoals necessary to achieve those goals. For example, an interviewer may have a goal of delivering an intervention if necessary for the subject to reach a desired health assessment score. Similarly, the interviewer may have the goal of reaching targeted measures for reciprocity, or other objective measures, during the live interaction with the subject.

Preferably, health assessment scores are used as the measure of effective progress through the use case and as indicators of where in the use case process the subject is. For example, an improved health assessment score typically suggests that the subject is at a stage in the use case that is closer to (rather than further from) one of the goals. As another example, an improved anxiety score typically suggests that the subject has received the benefit from some changed circumstance, e.g., a call back interview for a job with weekends free, which is one of the subject's goals or an intermediate step towards one of those goals.

By contrast, a prolonged lack of progress on health assessments may lead to a determination that the use case overall may not be attainable and/or should be augmented or changed. A drastic negative change in the caregiver's health assessment may occur because the caregiver herself has learned of a personal, life-threatening illness. In that case, it may be appropriate to modify the use case from effectively managing the care of an elderly parent while progressing through the logistics of health insurance claims associated with providing that care, to finding a substitute caregiver for an elderly relative while finding the best course of medical treatment for the original caregiver's personal health issues.

FIG. 1 is a high-level block diagram of language-related information databases usable by AI computational tools to execute certain steps of a preferred embodiment of the present invention. A controller 105 (also referred to as an "instance manager"), establishes global database 110 and a user database 150. Global database 110 is also referred to as "global predicate store" 110. Predicates have a central role in the AI computational operations of the inventive method. Note that the terms "predicate store" and "database" may be used interchangeably in the description of the invention.

Use case predicates 115 are a collection of predicates, that is, a collection of fact types (the "predicate head," for example, color), together with type arguments (the "predicate argument," for example, yellow), and conditions that controller 105 has determined are most relevant to the present use case. In the exemplary use case of managing the care of an elderly parent while progressing through the logistics of health insurance claims associated with providing that care, relevant predicates may include predicate head "insurance company," and predicate argument, "Acme Insurance Company. Also, in preferred embodiments global predicate store 110 contains information that is pertinent to more than one use case, and controller 105 determines what subset of that information will be used to define the scope of, and to manage, a particular use case.

Global predicate store 110 includes tokenized words for goals, conflicts and steps 120 that are relevant to the instant use case, and underly the predicate sets. "Goals" are the goals desirable for satisfactorily traversing the use case. "Conflicts" stem from goals that inhibit one another or are mutually exclusive. For example, a goal may be obtaining a work schedule with weekends off. A conflict may be the conflicting goals of having Sundays free to care for the elderly parent and having Sundays available to play golf. "Steps" are actions that are required or desirable to advance towards and accomplish goals. Global predicate store 110 also includes related predicate sets 125. Related predicate sets 125 are related to the use case, and also related to each other. The related predicate sets 125 may be organized by topic or activity or skill or by other logic that the probabilistic programming logic uses as determined for the use case. As examples, related predicate sets 125 may be scheduling predicates, skill predicates, step (protocol) predicates (e.g., a coaching or treatment method), goal predicates, goal predicates for steps, and goal predicates for the use case.

Global predicate store 110 further includes classifier scores 130, extractions 135, and other featurized data 140. As will be described in more detail, classifier scores are values reflecting a health assessment state. For example, a classifier score may be a score for anxiety level associated with the clinically recognized GAD health assessment. AI language analysis methods determine classifier scores, which process will be described in more detail. Classifier scores can be the predicate arguments of, or values associated with, predicate sets that are relevant to a subject's emotional state of mind, or the anticipated or desired state, or the like. Extractions 135 are preferably portions of actual language source, such as text, audio and video, that are the basis for at least some of the other contents of global predicate store 110, (i.e., use case predicates 115, goals, conflicts and steps 120, related predicate sets 125, and classifier scores 130). Other featurized data 140, as explained above with respect to the term "featurized," are other additional feature elements of language-related information that may serve as basis for the content of global predicate store 110. Other featurized data 140 may also include featurized information that is not derived from language communications. In addition to language-based features, non-language-based features also may be stored in global and user stores, to determine correlations between language and non-language facts. Examples of non-language-based features are data received from other machines about the user that may include measurements and scores for biological or other human functions, such as blood pressure or heart rate. These could be supplied by a wearable device, such as a glucometer or pedometer. The purposes of such correlations vary from determining how true an utterance may be given contrary facts, such as the blood pressure example, or to help determine patterns or degrees of truthfulness when certain topics are discussed. Thus, the language analysis is improved by the presence of non-language facts already featurized and stored in the stores. Global predicate store 110 contains the language-related information that is relevant, as determined by system controller 105, for the particular use case instance. The language-related information, among many other sources as will be described, is acted upon by AI computational tools to carry out aspects of a preferred embodiments of the present invention.

User predicate store 150 is a database comprising a subset of language related information as is stored in global predicate store 110. There is a unique user predicate store organized in the same fashion as user predicate store 150 for each user of the system. A user may be participating in more than one use case. Therefore, user predicate store 150 may include subsets of language related information corresponding to more than one use case. Controller 105 determines what information in user predicate store 150 is involved in analysis and management as to any give use case. The contents of user predicate database 150 are also initially established and continually managed by the system controller 105. Specifically, user predicate store 150 includes use case predicates 155, tokenized words for key goals, conflicts and steps 160, related predicate sets 165, classifier scores 170, extractions 175 and other featurized data 180. It is important to recognize that each user predicate store contains use case predicates 155, tokenized words for key goals, conflicts and steps 160, related predicate sets 165, classifier scores 170, extractions 175 and other featurized data 180 that are respective subsets of the corresponding content in global predicate store 110. Specifically, it is the subset of that content that has been determined to be relevant to the particular user during prior and current interactions with the user. Therefore, the content of user predicate store 150 differs from that of global predicate store 110, in that it is specific to a particular subject. For example, one user's individual predicate store 150 may have the predicate "0.95::drives (user124,car)", and yet another user's individual predicate store 1220 may have the predicate ""0.00:: drives (user123,car)", whereas global predicate store 110 may require one user who can drive to drive another user who cannot. In this manner, the global predicate store is applicable to all subjects involved in the same kind of use case (e.g., driving someone who can't drive but perhaps who has to appear in person and thus needs transportation in order to sign for medication). In a preferred embodiment, the system itself is also a user, and as other users, the system has a user predicate store 150 that is subject to rules established by controller 105 and reflected in global predicate store 110 for the use case.

Global predicate store 110 and user predicate store 150 (for each user) are established and managed by AI computational tools using probabilistic programming. Global predicate store 110 contains a super set of predicates, including conditions and rules for the use case, that are set by a controller (controller 105 described more fully with reference to FIG. 1). The conditions and rules are then applied by the probabilistic programming language to other predicates in global predicate store 110 as well as to predicates found in user predicate store 150 for users specified in the use case by controller 105. This management of global and user predicates occurs during live operation of the use case, which incorporates all use case predicates for all users specified by controller 105, and their attendant conditions. For instance, a predicate in global predicate store 110 may be "patients and doctors meet at 9 am daily except Monday" whereas a predicate in user predicate store 150 in this same use case may be "X meets with doctor daily except Monday". This could be expressed in Problog code as scheduled_event(meets (A, B), time_exception(weekly, monday)) WHERE is_a(A, doctor) and is_a(B, patient) [global kb example code] and scheduled_event(meets (Dr. Ali, user123), time_exception(weekly, monday)) [individual kb example code]. After the individual meets with the doctor on Tuesday, global predicate store 110 and user predicate store 150 are updated, as per this example event_occurred(meets (Dr. Ali, user123), date(Tuesday, Oct. 20, 2020)) [global predicate example code] and [user predicate code example]. As illustrated, the condition, "except Mondays", is used logically by the probabilistic programming in its determinations.

Figure 2:
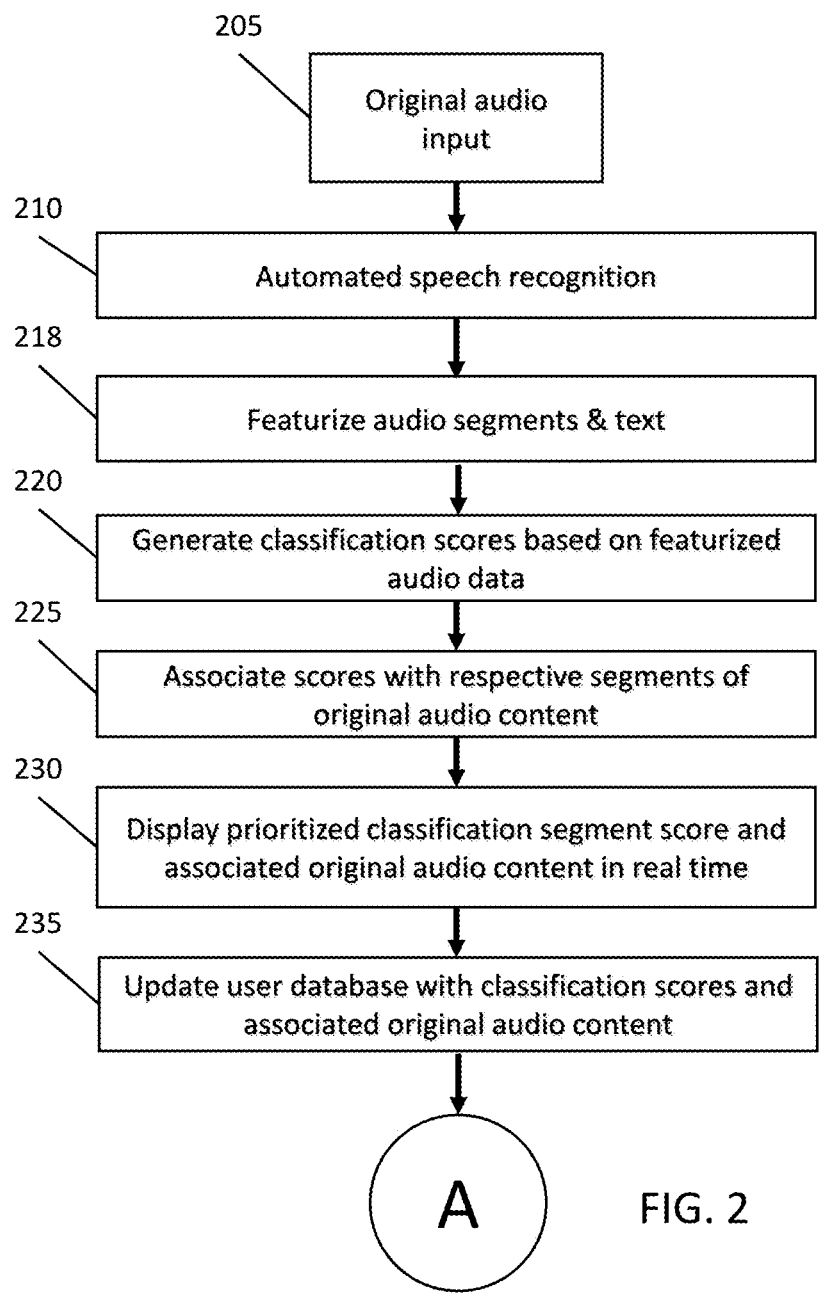
FIG. 2 is a flow diagram illustrating steps of an automated method for an interactive care system in accordance with various embodiments of the present invention.

FIG. 2 is a high-level block flow chart of a preferred method according to the present invention. First, a discussion of each step of the method will be presented at a high level. Subsequently two additional methods will be presented a high level. Detail with be provided regarding the activity of each step with reference to further detailed drawings.

The illustrated method productively guides a conversation between a subject, such as the caregiver of an ill family member, and an interviewer, such as a nurse. Based on language analysis that will be described in detail, the interviewer is supplied in real time with on-screen natural language support interaction guidance. The system generates and displays a recommendation to the interviewer of what to discuss in the conversation that is likely to comfort or otherwise assist the subject.

At step 205, original audio is input into the system. This audio input may be in the form of sound, electrical signals, digital representations, and the like. This audio may represent the audio of a phone call between a subject, in the earlier referred-to example, the caregiver, and an interviewer, the nurse whom the subject has been referred to by the insurance company.

At step 210, the audio input is analyzed by a language featurization system. In the preferred embodiment, the language featurization system comprises automated speech recognition functionality, text based natural language processing functionality, and audio signal processing functionality. The language featurization system featurizes the original audio input at step 218. The featurization preferably produces at least i) a text transcript of the audio, ii) audio broken down into audio segments which may represent individual utterances, sentences, or sentence fragments, with the segments tagged to identify the speaker, iii) tokens which represent individual words, iv) ngrams which represent word combinations that, when taken together have a common meaning apart from what the words would mean individually, iv) word vectors associated with the tokens and ngrams, which represent a token or ngram together with its potential substitutes such as synonyms, with the vectors tagged to identify the speaker v) sound features such as loudness, loudness range, power, peak-to-average power ratio, and pitch characteristics including centroid, crest, flatness, kurtosis, roll-off, skewness, slope and spread, and vi) formatted third party data such as named entities including persons, places, and brands.

At step 220 health-assessment-related classification scores for audio segments are generated based upon the featurized data. For example, a particular loudness range combined with certain specific words represented by tokens and vectors may indicate a high anxiety level. For example, the featurized data associated with an audio segment utterance about a bank account balance may indicate both a high anxiety level and a poor QoL outlook. By correlating the available scores in can be determined that the subject is worried about finances.

A classifier may be trained to identify such instances and assign a health assessment score to the associated audio segment accordingly. For example, at step 220 the classifier scores incoming featurized data and associated audio segments for anxiety level.

At step 225, the classification scores form part of an "extracted" predicate set associated with a particular audio segment. Other predicates are extracted from the audio feed, including those that do not relate to a health assessments that would be scored by the classifier. For example, objective fact related predicates, such as predicate head "subject's age" and predicate argument "55."

At step 230, preferably in real time during the conversation, a representation of a chosen classification, such as an anxiety level, is displayed to the interviewer on a rolling basis. This is paired with the display of the audio content transcribed text that reflects the associated audio segment that was part of the basis of the classifier score. This dual display allows the interviewer to be aware of the nature of the discussion that affected the subject's classification score.

At step 235, user predicate store 150 is updated with the featurized data produced by the language featurization system, as well as the classification scores, extractions, and predicate sets to reflect the subject's then-most current status and situational context.

Optionally at step 235, a comparison is made between the recently obtained language data and that of user predicate store 150. If it is determined that there is not sufficient correlation between the two, then a preliminary determination is made that the subject involved in the phone conversation is not the user associated with that user predicate store. In that case, a new user predicate store is created. The system regularly checks for that correlation as potential updates to each predicate store are made available to determine if in fact they relate to the same user. This involves processes known in the art as diarization and entity resolution.

In addition, at step 235 global predicate store 110 is updated with that subset of recently obtained language information that is pertinent to the use case. The foregoing novel language analysis method can be specifically integrated into an anxiety management application, where is it particularly useful because typical use cases tend to be anxiety provoking.

Figure 3:
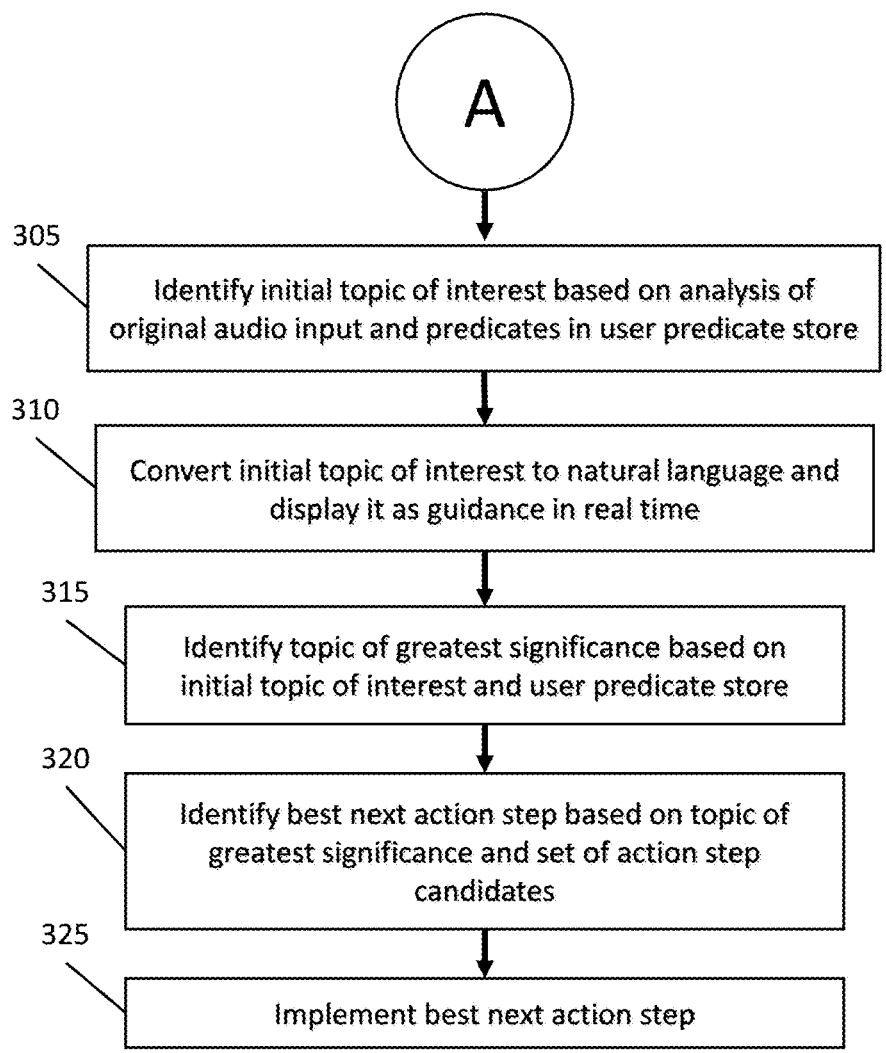
FIG. 3 is a flow diagram illustrating steps of an automated method for an interactive care system in accordance with various embodiments of the present invention.

Turning to FIG. 3, at step 305 an initial topic of interest may be identified for each audio segment of each speaker for which there is a classifier score. The extracted predicate sets and related features associated with the classification scores of one or more classifiers that renders a score on the audio segment are used to surface one or more topic candidates for each audio segment. These one or more topics for each audio segment are ranked according to rules established by controller 105 to determine which topic candidate surfaced by the extractions associated with the classifier scores is the initial topic of interest for each scored audio segment. For example, depending on the rules established by the controller, if high anxiety has been surfaced in connection with a discussion of finances, it may receive a relatively higher score indicating a relatively higher level of concern. Alternatively, if high emotional Quality of life surfaced in connection with a discussion of an event, it would receive a relatively higher score indicating a relatively higher level of satisfaction.

These topics correlate to the score rendered by the health classifier or other classifier for a given audio segment. The topic may be one of immediate concern to the speaker or alternatively, one of immediate satisfaction to the speaker. Or the topic may be one of neither concern nor satisfaction as measured by a score. If the audio segment is not scored above a threshold determined by the use case, the audio segment has no reported score for a topic that still may be present and stored as predicates in the user store for other uses by the system.

Since conversation involves multiple audio segments, a stream of scores and associated topics may be produced during any one conversation. Moreover, since multiple classifiers run concurrently over the same audio segments, multiple different scores for different classifiers for the same audio segments are rendered concurrently. These streaming concurrences likely yield a plurality of scores for any one audio segment, and occasions the need for a mechanism to determine 1) which scores or correlated scores matter most in the immediate context associated with the audio segment 2) which scores matter most in the short term context associated with the overall conversation and 3) which scores matter most in the longer term context of the use case itself.

The controlling mechanism for determining which classifier scores or correlations of scores matter most in each respective context is determined by rules established for the use case and controller 105. Similarly, which topics likely surfaced by scores matter most in the respective context are also determined by rules established for the use case and use case users using the controller. For example, the controller may create a matrix of scores and correlations between them by context to determine which topics associated with, respectively, an audio segment, a conversation, and the goals of a use case are prioritized. Alternatively, use case rules for handling concurrent scores may include algorithms that formalize the relationships observed between correlated scores and which topics to then surface provided scores above a threshold, running averages for scores and the repetition or frequency of repetition of similar or dissimilar topics correlated to scores above a threshold, or other means by which use case rules may be applied to scores and associated topics surfaced during audio segments and/or the running discussion.

At step 310, the rules established by the controller for selecting topics of interest are applied, and the winning candidate using rules for the use case is converted to natural language to support the interactive goal setting and attainment between participants and displayed to the interviewer in real time. A stream of topics per above may thus be displayed during a conversation showing associated scores using rules established by the controller for their calculation and/or display or text to speech.

For example, if the topic of "bank account balance" indicated a very high level of anxiety, the interview might be guided with displayed natural language text to remind the subject that an insurance reimbursement check is on the way. If at another point in the conversation the topic of "time with my family" indicated a very high quality of life, the interview might be guided with displayed natural language text to remind the subject that the reimbursement check also covers paid-time-off. These could appear in natural language as a list, "anxious about finances, happy to spend time with family . . . " together creating a string of displayed narrative segments associated with streaming audio segments and classifier scores and rules for display. This provides the interviewer with a fuller understanding of the subject's immediate context as well as the short-term context of the conversation. The display also allows the interview to learn when changes in narrative, or topic changes, correlate to changes in classifier scores.

The method of producing step 310 natural language from winning candidate topics surfaced from extractions associated with one or more classifier scores for each audio segment is more fully described in connection with FIG. 13.

At step 315, a topic of greatest significance is identified by comparing and ranking main topics of interest from step 305 for each audio segment and the topic or topics associated with the user's traversal of the use case overall. From predicate stores 110 and 150 graphs representing each step along the overall use case path, and the subject's location along that path, are produced and, preferably, displayed to a user. Nearby steps are ranked according to rules set by controller 105 for the use case, and the highest ranking next step is identified. For example, it may be that finances are most troubling at the very moment to the user; however, taking the action of finding a job that has weekends free is overall more important to success in the use case, and the job search topic is ranked highest. Step 315 thus uses rules set by controller 105 to determine which of the many contexts and their associated topics are most significant.

At step 320, information domains defined by controller 105 are searched for content describing and facilitating actions that will advance the subject in the area of the identified topic of most significance. Rules defined by controller 105 determine which action step discovered is considered the most productive next action step.

At step 325, the most productive, or best next action step, is communicated to the subject.

As described by the foregoing, the particular preferred method effectively guides the interviewer to make the immediate conversation with the subject more productive based on novel applications of AI-based language analysis. In addition, the subject receives the suggestion for an action or actions which will be most useful to engage in next, in order to traverse and resolve the use case.

Figure 4:
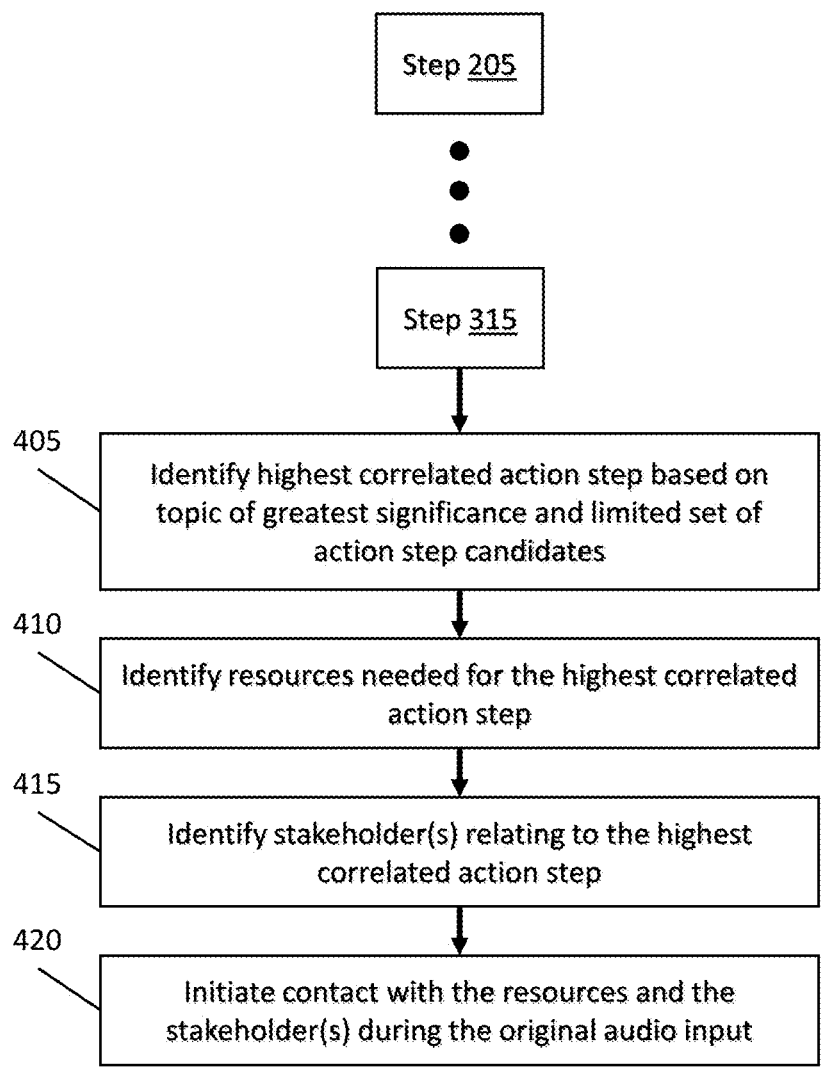
FIG. 4 is a flow diagram illustrating steps of an automated method for accomplishing a next action step in accordance with various embodiments of the present invention.

FIG. 4 represents a particular preferred version of the inventive method that focuses on coordinating resources and stakeholders associated with the next best step, in a novel and unconventional way. Specifically, the method of FIG. 4 is identical to that of FIGS. 2 and 3 except for the novel and unconventional steps 405, 410, 415, and 420.

More specifically, at step 405 information domains defined by controller 105 are searched for content describing and facilitating actions that will advance the subject in the area of the identified topic of most significance. Rules defined by controller 105 determine which action step discovered is considered most productive. What is particularly novel about this preferred version of the method, is that the rules set by controller 105 limit the selection of the most productive action step to one that i) has contact information available for the resource(s) that are required, ii) involves resources that can be marshalled immediately, and iii) involves a third party stakeholder who can also be contacted immediately, and who is in a position to supervise the execution of the action step. An example of the inventive method initiating such an action step is as follows: A pharmacy that can fill a prescription for the subject is identified, that pharmacy is contacted to fill that prescription, a transportation service is identified and contacted to transport the subject to the pharmacy, a family member of the subject is identified and advised that the subject will be picking up the required prescription, including when, where, and how.

At the next step 410, the resources fitting the foregoing criteria are identified.

At the next step 415, the stakeholder(s) fitting the foregoing criteria are identified.

And, at the next step 420, the resources and stakeholder(s) are contacted in real time during the ongoing conversation between the interviewer and the subject.

Figure 5B:
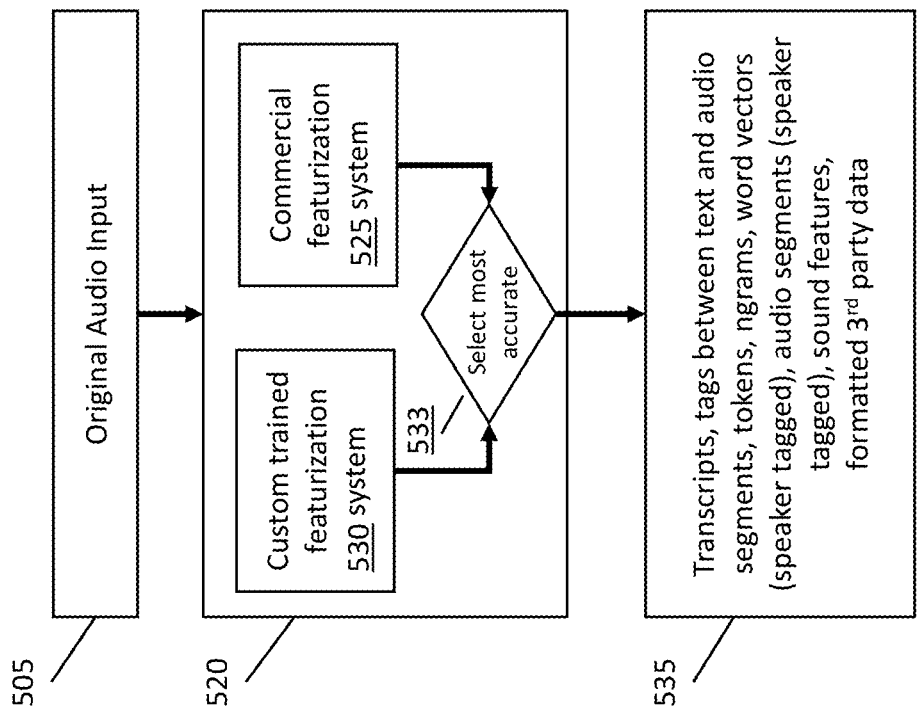
FIG. 5B is a flow diagram illustrating steps of an automated method for featurizing audio input in accordance with various embodiments of the present invention.
Figure 5A:
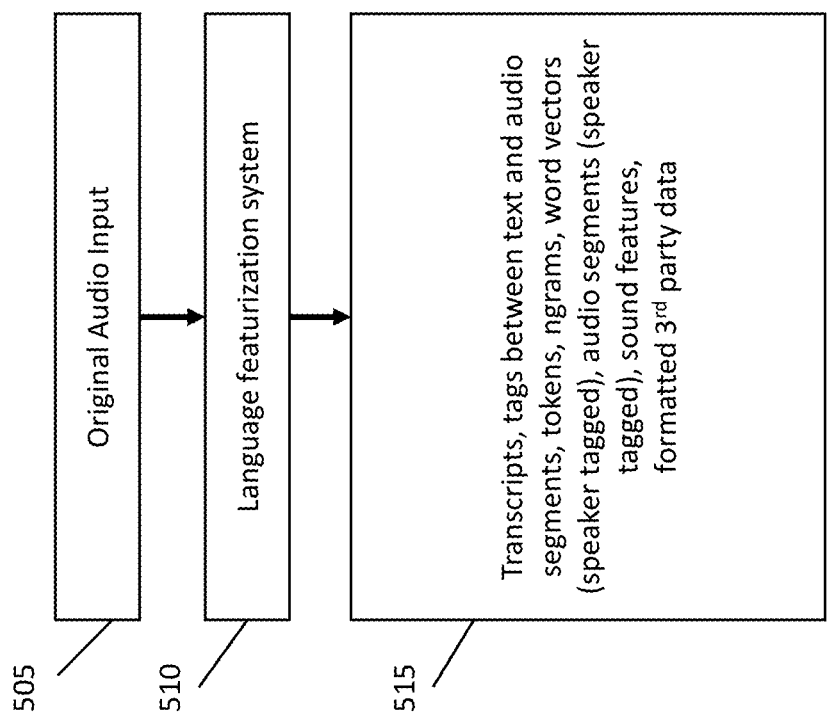
FIG. 5A is a flow diagram illustrating steps of an automated method for featurizing audio input in accordance with various embodiments of the present invention.

FIG. 5A and FIG. 5B provide additional detail for step 205. Specifically, referring to FIG. 5A, original audio input is received at step 505. As an example, this may be the audio associated with a phone conversation between a caregiver (subject) and a nurse (interviewer). At step 510, original audio input is received by a language featurization system that comprises automated speech recognition functionality, text based natural language processing functionality, and audio signal processing functionality. The language featurization system may comprise only readily available language and audio processing elements, as will be appreciated by one skilled in the art. Alternatively, according to the preferred embodiment, the language featurization system may be a novel customized system as will be more fully described in connection with FIG. 5B.

At step 515, the language featurization system featurizes the received audio input, generating at least, i) a text transcript of the audio, ii) audio broken down into audio segments which may represent individual utterances, sentence or sentence fragments, the segments tagged to identify the speaker, iii) tokens which represent individual words, iv) ngrams which represent word combinations that when taken together have a common meaning apart from what the words would mean individually, iv) word vectors associated with the tokens and ngrams, which represent a token or ngram together with its potential substitutes such as synonyms, the vectors tagged to identify the speaker, v) sound features such as loudness, loudness range, power, peak-to-average power ration, pitch characteristics including centroid, crest, flatness, kurtosis, roll-off, skewness, slope and spread, and vi) formatted third party data such as named entities including persons, places, and brands. The featurized data is stored electronically so as to be accessible to the rest of the system during the execution of the method.

In comparison, FIG. 5B illustrates an alternative embodiment of step 520 that involves at least two language featurization systems, system 525 and system 530. In this representative embodiment, system 525 may comprise commercially available automated speech recognition functionality, text based natural language processing functionality, and audio signal processing functionality.

In addition, this version of the inventive method includes custom trained language featurization system 530. Specifically, as will be more fully described, language featurization system 530 is trained using audio content taken from a large collection of conversations that i) are similar in nature to common use cases involving, for example, older subjects and medically related use cases, and ii) occur during a clinical trial intervention before which and after which subjects in the clinical trial are tested using clinically validated health assessments (e.g., GAD). This audio content can be referred to as "reference audio content" or "reference speech data." The classifier subsystem and classifier functionality that generates scores associated with health assessment may be trained on the same reference speech data. Training based on the particularly pertinent reference speech data allows the custom language featurization system to more reliably "understand" and, therefore, better featurize original audio input, as compared to a language featurization system comprising only commercially automated speech recognition functionality, text based natural language processing functionality, and audio signal processing functionality.

At step 533, the running outputs of language featurization systems 525 and 530 are measured by the language featurization systems functionality for confidence level with respect to calculated features and text transcription, and the featurization data found most accurate is included in the featurized output at step 535.

Figure 6:
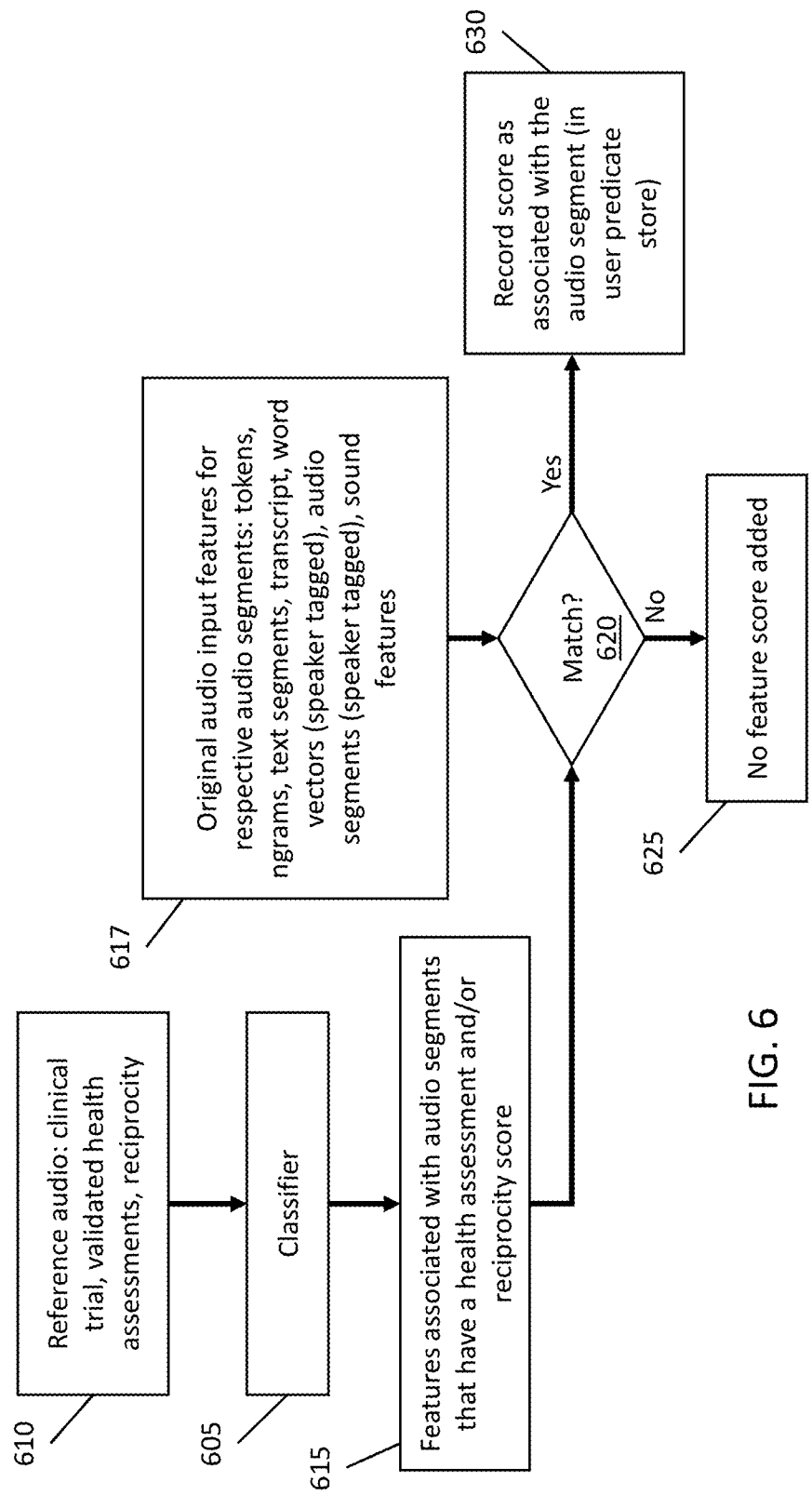
FIG. 6 is a flow diagram illustrating steps of an automated method for assigning category classification scores in accordance with various embodiments of the present invention.

FIG. 6 provides further detail relating to step 220 shown in FIG. 2. Specifically, FIG. 6 illustrates the generation of health assessment scores for audio segments that merit such a score. As generally described, each audio segment from the original audio input has associated featurized feature data. In addition, a classifier subsystem has been trained on the reference speech data to recognize what audio segment feature data indicates a health assessment score, and what the magnitude (value) of that score should be.

For example, the reference speech data which has been used to train a classifier that scores anxiety may reflect that when a subject utters the phrase "bank account balance," or something similar as reflected by the word vectors of those particular words, and that utterance has a particular loudness range (a feature of the utterance), the subject is recognized to be anxious above a specified measurable threshold. The classifier retains that relationship data so that when similar features are found associated with similar utterances in original audio input, that audio segment should be scored for anxiety at a corresponding score level.

Note that the classifier may be trained not only on reference speech data, but also via custom speech analysis that intelligently identifies additional characteristics of speech. One example that will be more fully described is "reciprocity." Reciprocity reflects how similar the subject's utterances are to the interviewer's utterances. Reciprocity is often an indicator of the productiveness of a conversation. Reciprocity in a conversation between two parties has been detected in a novel and inventive manner according to the present invention. The classifier function in FIG. 6 is trained to recognize reciprocity from the features of the original audio input segments.

Referring to FIG. 6, classifier 605 preferably has been trained on reference speech data which comprises audio content from clinical trials that have associated clinically recognized health assessments such as GAD and/or QoL measures, or the like. Specifically, the reference speech data has been scored on the clinically recognized health assessments (e.g. GAD) before and after the clinical intervention of the clinical trials. Preferably, classifier 605 also has been trained to recognize other characteristics, in this example, reciprocity.

The classifier functionality of classifier 605 included hashmaps of the language feature sets that merit health assessment and reciprocity scores. Hashmaps will be recognized by those skilled in the art as a basis for comparing sets of digitally represented information to one another. A hashmap is a data structure that allows very fast storage and lookup of a numeric score for any input piece of information (e.g., a token and ngram). At step 615, those hashmaps are made available for determining if there is a match between an extractor and/or classifier and the incoming featurized data. The hashmaps may contain a feature (label) and a value (score) for each feature.

At step 617, similar hashmaps are made available for each original audio input audio segment feature set.

At comparison step 620, the hashmaps from the classifier are compared to each audio segment feature set to determine whether that segment merits a health assessment score or reciprocity score, and what the value of that score should be.

At step 620, if the hashmaps do not match, then no score is associated with that original audio input segment, shown at step 625. If the hashmaps match, then the score is recorded as associated with the particular segment, shown at step 630. Preferably, the scoring is ongoing, or "rolling," in real time, allowing for real-time display of health assessment scores and associated segment transcripts.

Figure 7:
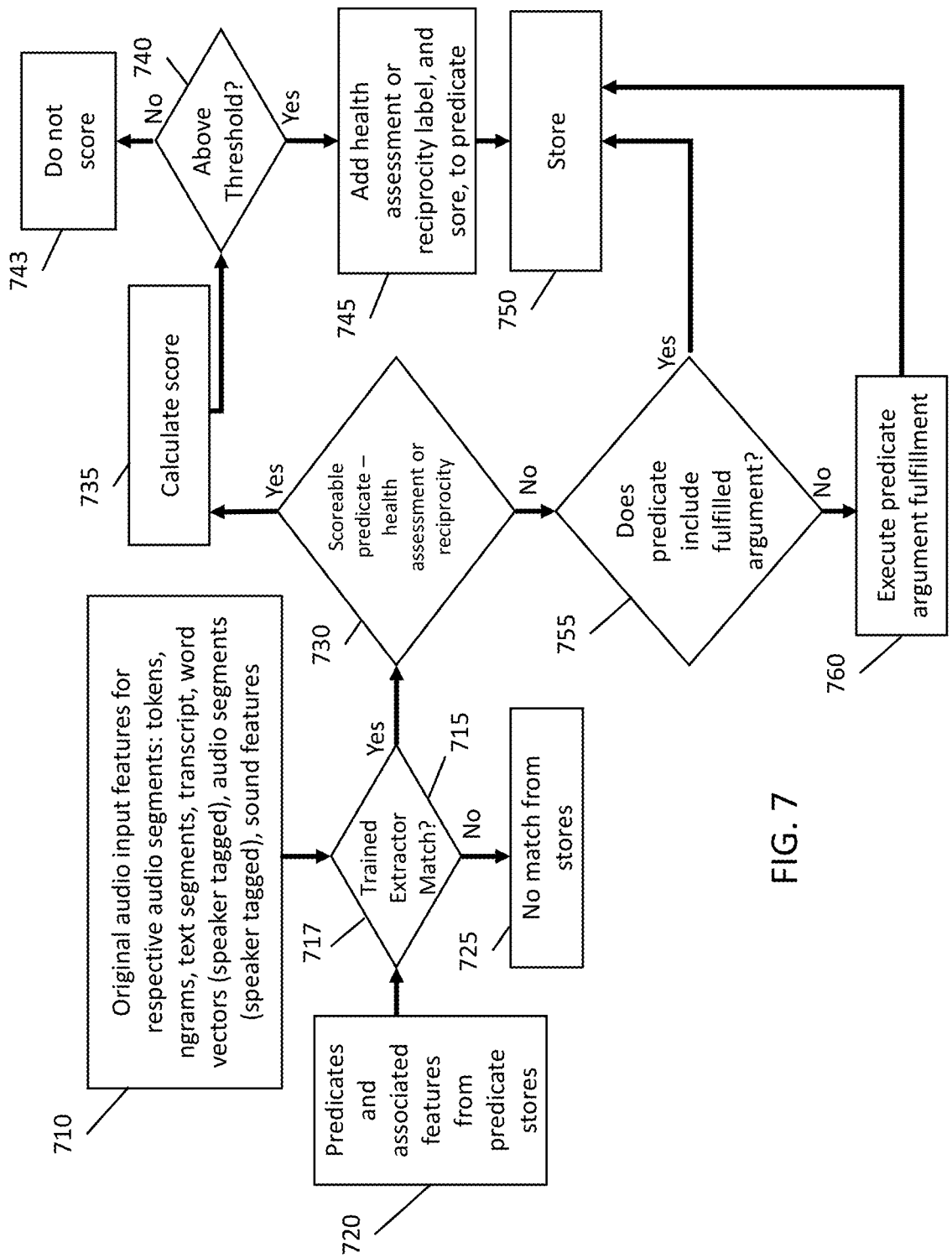
FIG. 7 is a flow diagram illustrating steps of an automated method for extracting information from received audio input data and assigning category classifications scores to portions of language input in accordance with various embodiments of the present invention.

FIG. 7 illustrates how predicate sets are developed from the incoming original audio input audio segments. In addition, FIG. 7 illustrates how the health assessment scores determined as shown in FIG. 6 are applied to the predicate sets developed from the incoming original audio input segments. The functionality shown in FIG. 7 facilitates step 225 of FIG. 2. Specifically, classifier 605 generates health classification scores with original audio input audio content, including the predicate sets that are generated from that content.

Specifically, at block 710, the featurized data of each original audio input audio segment is made available to comparator 715. Similarly, at block 720 the featurized data associated with the already identified predicate sets that reside in the global and user predicate stores 110 and 150 respectively, is made available to comparator 715.

Comparator 715 includes trained predicate extractor 717. Trained predicate extractor 717 may be trained in part on the same reference speech data as the custom trained language featurization system and the health assessment classifier 605. Custom trained extractor 717 is central to the function illustrated by FIG. 7. Therefore, it is helpful to depart briefly from description of the process illustrated in FIG. 7, to further describe the custom training of classifier 605 and extractor 717.

Figure 8:
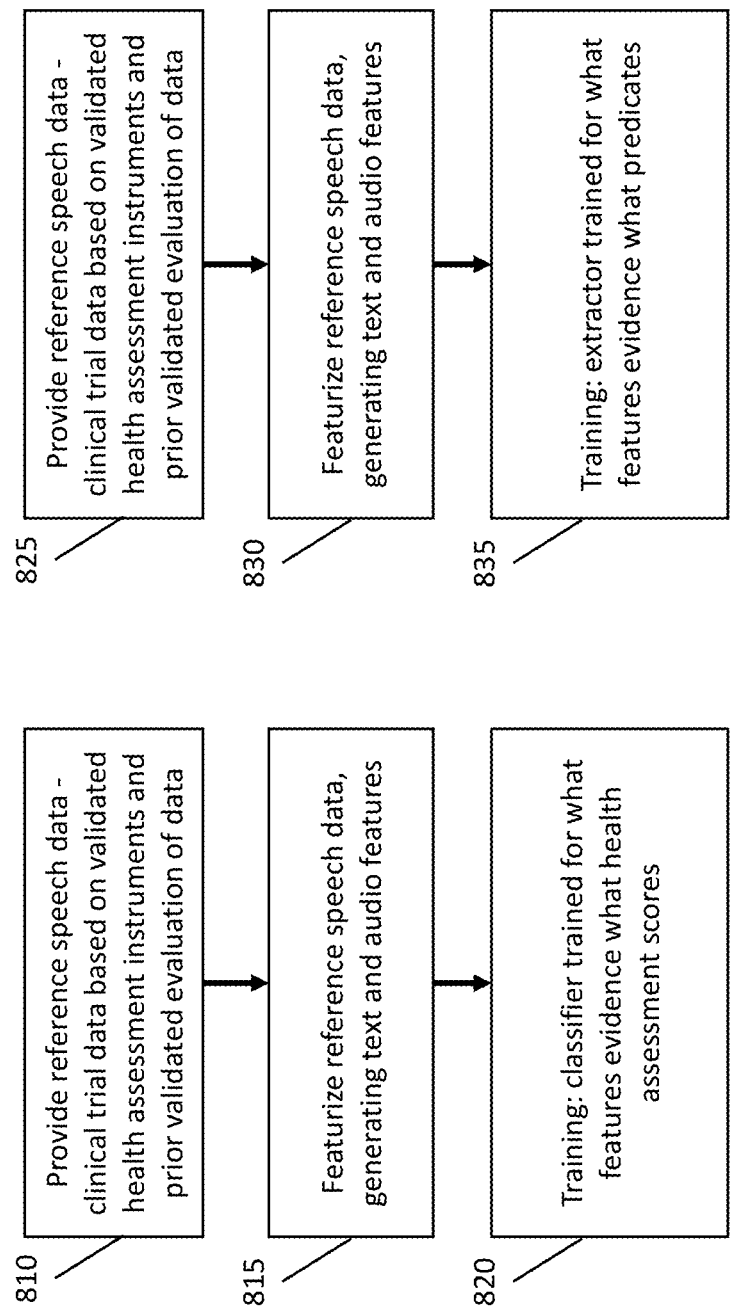
FIG. 8A is a flow diagram illustrating steps of an automated method for training a classifier in accordance with various embodiments of the present invention.
FIG. 8B is a flow diagram illustrating steps of an automated method for training an extractor in accordance with various embodiments of the present invention.

Reference is now made to FIGS. 8A and 8B. FIG. 8B illustrates the customized training of extractor 717, and FIG. 8A illustrates the customized training of classifier 605. Referring first to FIG. 8B, at step 825 the reference speech data is made available. As previously noted, the reference speech data is audio content taken from a large collection of conversations that i) are similar in nature to common use cases, involving for example older subjects and medically related use cases, and ii) which have associated clinical assessments for GAD and/or other clinically recognized health assessments, or the like. Specifically, the reference speech data has been scored on the clinically recognized health assessments (e.g., GAD) before and after the clinical intervention of the clinical trials.

At step 830, the reference speech data is featurized. Extractor 717 may be trained from the reference speech data. At step 835, to train extractor 717 on reference speech data, predicate sets that include predicate heads and predicate arguments are determined from the corresponding reference featurized data provided at step 830. Based on the reference speech data, the correlation is made to establish what language features result in particular predicate heads and predicate arguments. This information, what features indicate what predicate sets, is used by extractor 717 to compare to incoming features from language input.

Similarly, referring to FIG. 8B, at step 810, the reference speech data is made available. At step 815, the reference speech data is featurized. At step 820, to train classifier 605, health assessment scores are determined from the corresponding reference featurized data provided at step 815. Using a neural network, the reference speech, and pre and post clinical intervention health assessment scores to train a health assessment classifier, it is determined what language features result in particular health assessment scores, and their respective magnitudes (values). This information is compared by classifier 605 with incoming features from language input to classify that input. Relating to the custom training of classifier 605, reference has been made to scoring speech and conversation characteristics such as reciprocity. Preferably, classifier 605 is trained to not only apply health assessment scores to audio segments, but also reciprocity scores, and the like.

Figure 9:
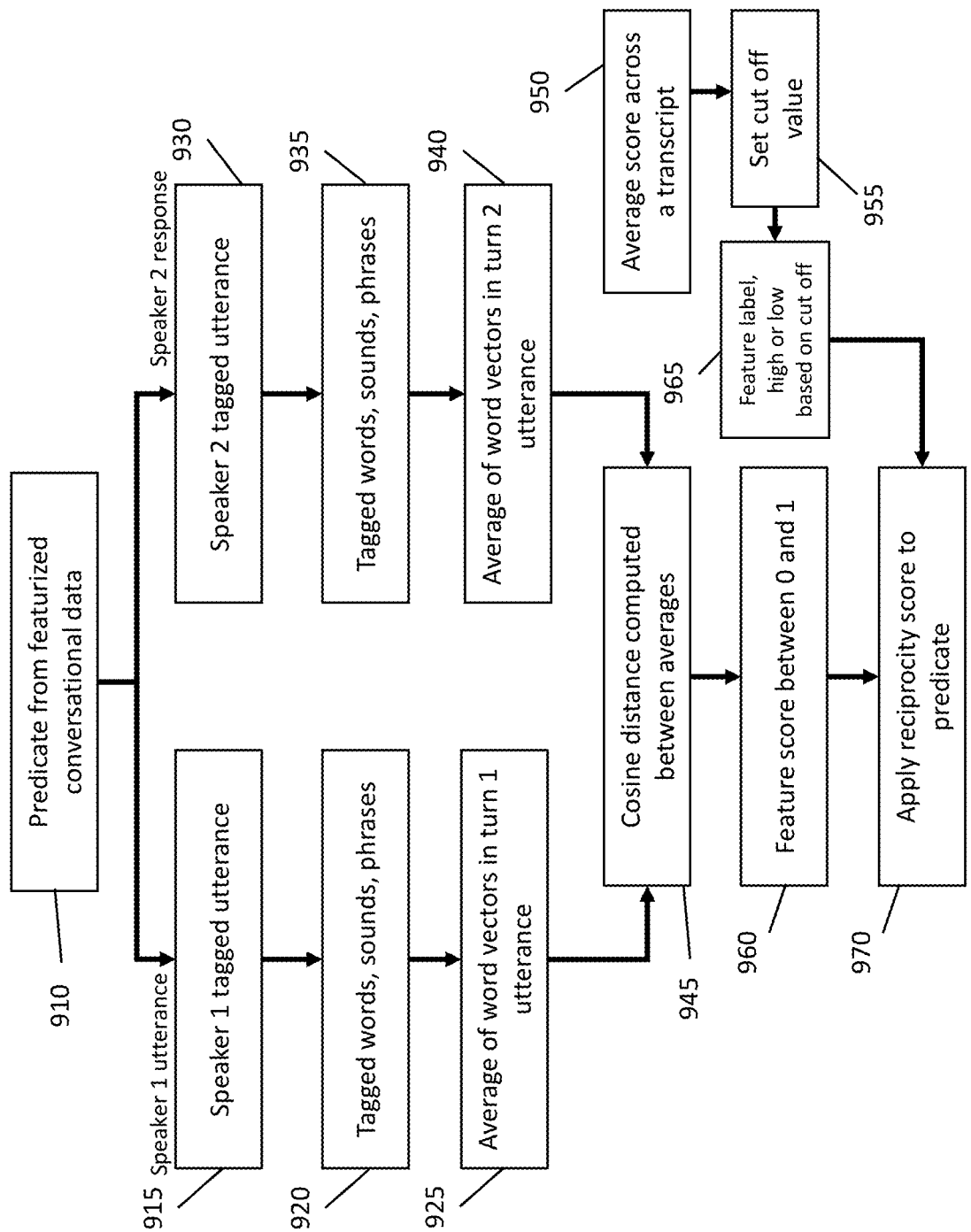
FIG. 9 is a flow diagram illustrating steps of an automated method for determining a reciprocity quality of a conversation in accordance with various embodiments of the present invention.

A process for detecting reciprocity is illustrated in FIG. 9. At step 910, the process begins with a predicate head extracted from a certain point in the featurized conversational data. The first speaker's utterance that is associated with the predicate is analyzed at steps 915, 920, and 925. Specifically, the utterance is identified at step 915 and the constituent words, sounds and phrases are detected at step 920. The word vectors associated with the words, sounds and phrases are mathematically averaged at step 925. The other speaker's responsive utterance is likewise analyzed at steps 930, 935, and 940.

To determine the degree of similarity between the two speakers' utterances, the cosine distance between their respective word vector averages is computed at step 945. At step 960, the cosine distance is converted into a reciprocity value. At step 950, the distribution of scores across the whole conversation (transcript) is tracked. This permits a cut off value to be determined at step 955 for high reciprocity (top quartile) and low reciprocity (bottom quartile). At step 965, these threshold values are applied to label the reciprocity feature as high, medium, or low. At step 970, the reciprocity score is added as a predicate. In this way, classifier 605 can be trained to recognize which language features are associated with reciprocity and reciprocity values.

Returning to FIG. 7, trained extractor 717 compares the features of predicates from stores 110 and 150 to features associated with the original audio input segments. If no match is found, then no predicate from the predicate stores is associated with that incoming audio segment in step 725. If a predicate match is identified, at step 730 a determination is made as to whether the predicate is one that is associated with a health assessment score or other classifier-based score such as reciprocity. If the predicate can be so scored, then at step 735 classifier 605 calculates the corresponding score based on language features associated with the predicate.

In step 740, it is determined whether the calculated score is above a threshold. If it is, then the relevant health assessment label, for example anxiety or QoL, and the associated score are added to the predicate as an argument at step 745. The predicate, including the new label and score, is stored at step 750. If at step 740, it is determined that the score is below the threshold, then the predicate is not labeled nor scored at step 743.

Returning to step 730, if the predicate is not of the type appropriate for a health assessment score, then at step 755 it is determined whether the predicate includes all of its expected predicate arguments. If it does, the predicate set is stored at step 750. If it does not, then at step 760 a predicate argument fulfillment process is executed, as illustrated by FIG. 10.

Figure 10:
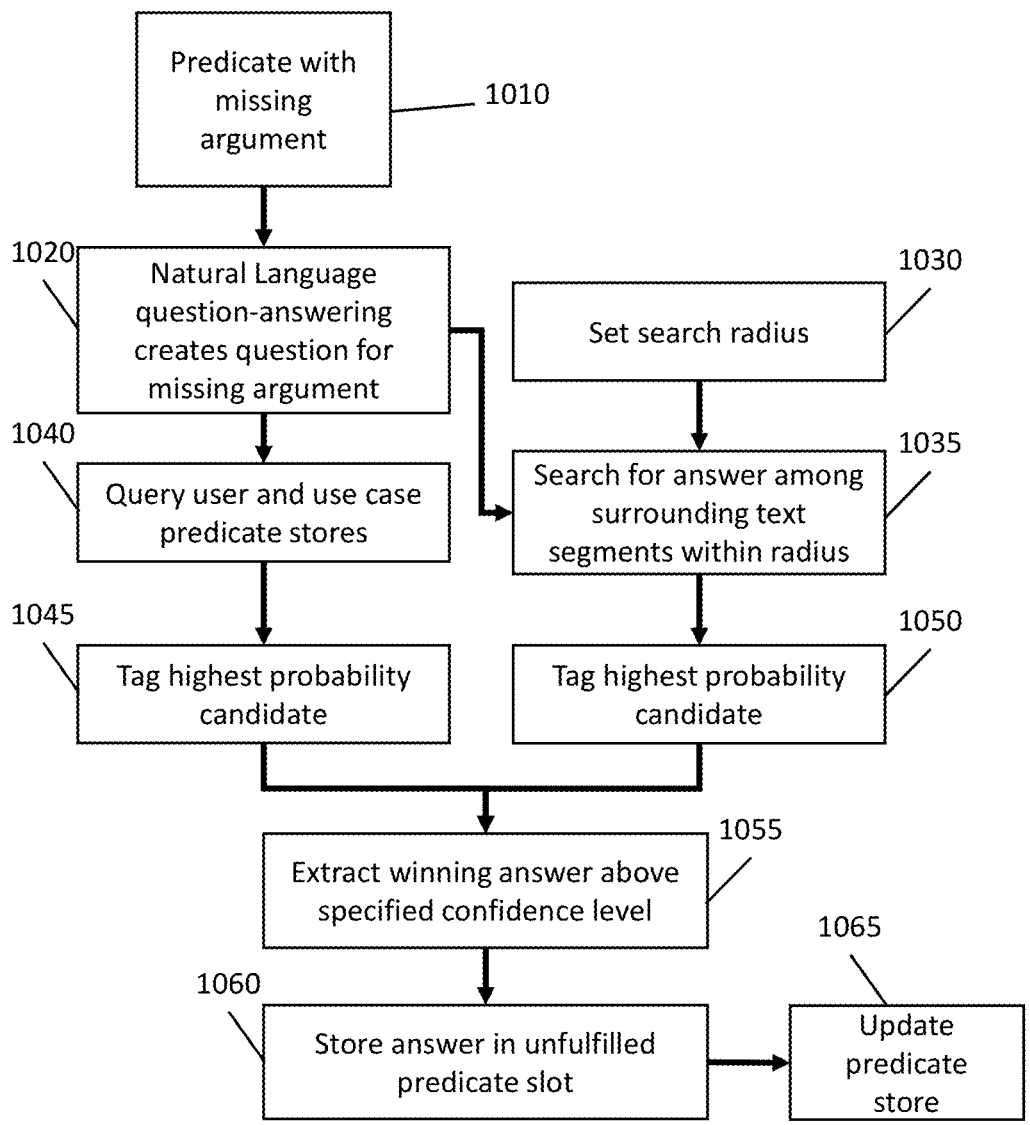
FIG. 10 is a flow diagram illustrating steps of an automated method for completing the predicate argument for a predicate header and argument set in accordance with various embodiments of the present invention.

Referring to FIG. 10, the predicate with the missing argument is provided at step 1010. At step 1020, known natural language question answering techniques are used to produce an appropriate question for searching for the missing predicate argument. Those techniques are used to query the user and use case predicate stores for an answer, and to search surrounding transcript text for an answer. At step 1030, a search radius is set for searching the surrounding text transcript. At step 1035, the surrounding text is searched, based on the question from step 1020, as limited by the radius from step 1030.

At step 1040, the question developed at step 1020 is used to query predicate stores 110 and 150 for probable argument values. Those values are ranked in confidence at step 1045 and the highest probability candidate chosen. Similarly, probable values from the text search at step 1035 are ranked in confidence at step 1050 and the highest probability candidate chosen.

At step 1055, the highest probability candidates from steps 1045 and 1055 having a confidence score above a predetermined threshold are ranked and the highest is selected for the unfulfilled predicate argument. The selected candidate is associated with the corresponding predicate set at step 1060. The predicate set is then stored at step 1065.

Thus, according to the foregoing description, predicate sets have been extracted from the original audio input segments based on respective featurized data and health assessment and reciprocity scores have been applied.

Figure 11:
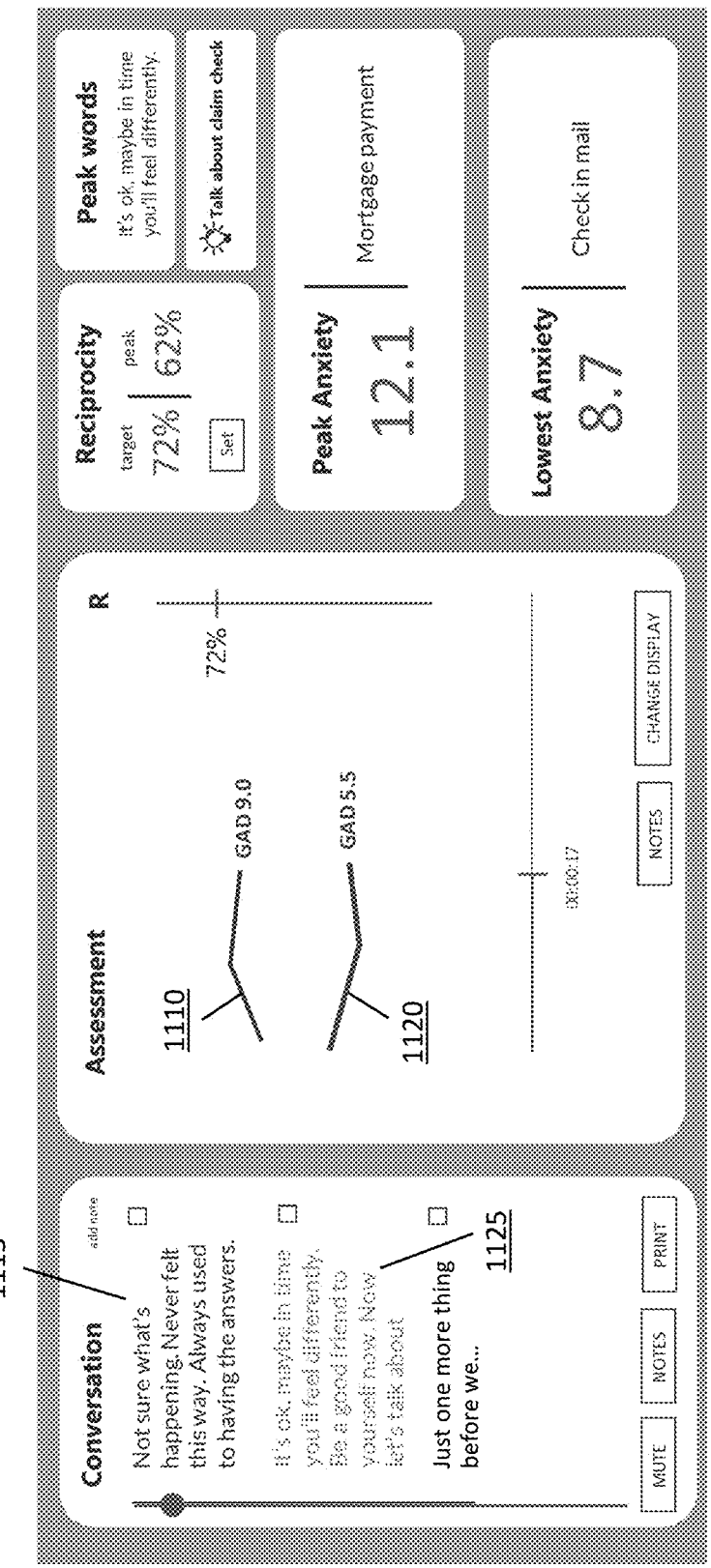
FIG. 11 is an illustration of a screen displaying classification scores and associated transcribed portions of a conversation in accordance with various embodiments of the present invention.

FIG. 11 corresponds to step 230 shown in FIGS. 2, 4 and 6. Specifically, FIG. 11 represents a display viewable by the interviewer during the original audio input conversation. For this feature of the inventive method, a particular priority health assessment category is selected, for example, anxiety.

Graph line 1110 represents the rolling anxiety score of the subject, as has been applied to each audio segment as explained in connection with FIGS. 9 and 10. Text portion 1115 is the transcription of the audio segment associated with the most recent score update to the graph. Graph 1120 represents the rolling anxiety score of the interviewer. Text portion 1125 is the transcription of the audio segment associated with the most recent score update to the graph. Access to this information in real time allows the interviewer to produce a more comforting and productive conversation.

Figure 12:
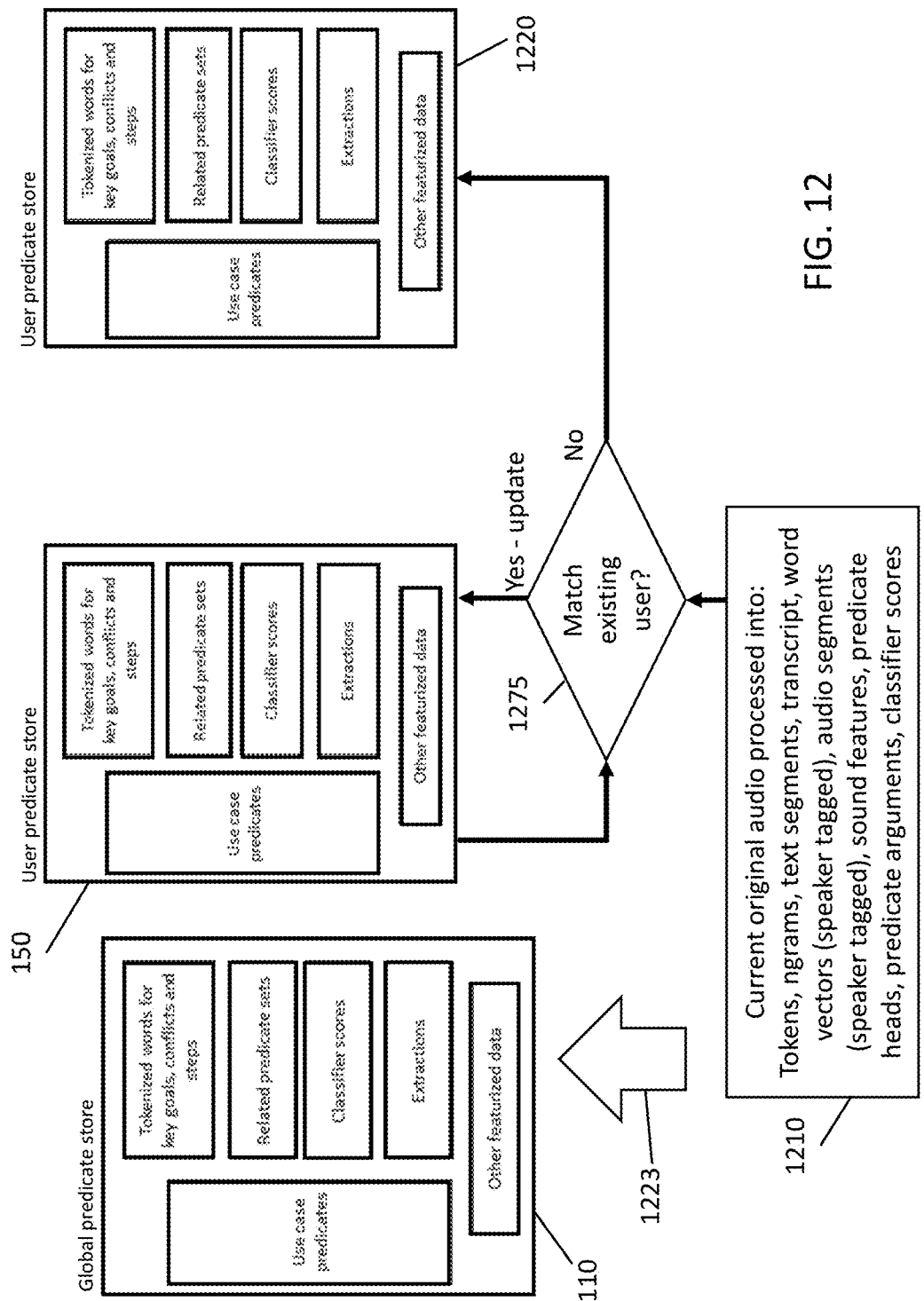
FIG. 12 is a flow diagram illustrating steps of an automated method for updating a use case database and a user database in accordance with various embodiments of the present invention.

FIG. 12 corresponds to step 235 shown in FIG. 2. As shown in FIG. 12, the featurized data, as well as classification scores, extractions, and predicate sets associated with the recent original audio input, are updated in user predicate store 150. This update modifies user predicate store 150 to reflect the subject's most current status and situational context. At step 1275, a comparison is first made between the recently obtained language data and that already stored in user predicate store 150. If it is determined that there is not sufficient correlation between the two, then a preliminary determination is made that the subject involved in the recent phone conversation is not the user associated with user predicate store 110. In that case, a new user predicate store 1220 is created. The system regularly checks for that correlation as updates to each predicate store are made, to determine if in fact they relate to the same user.

Preferably, global predicate store 110 is updated, as reflected by arrow 1223, with that subset of recently obtained language information that is pertinent to the use case.

Figure 13:
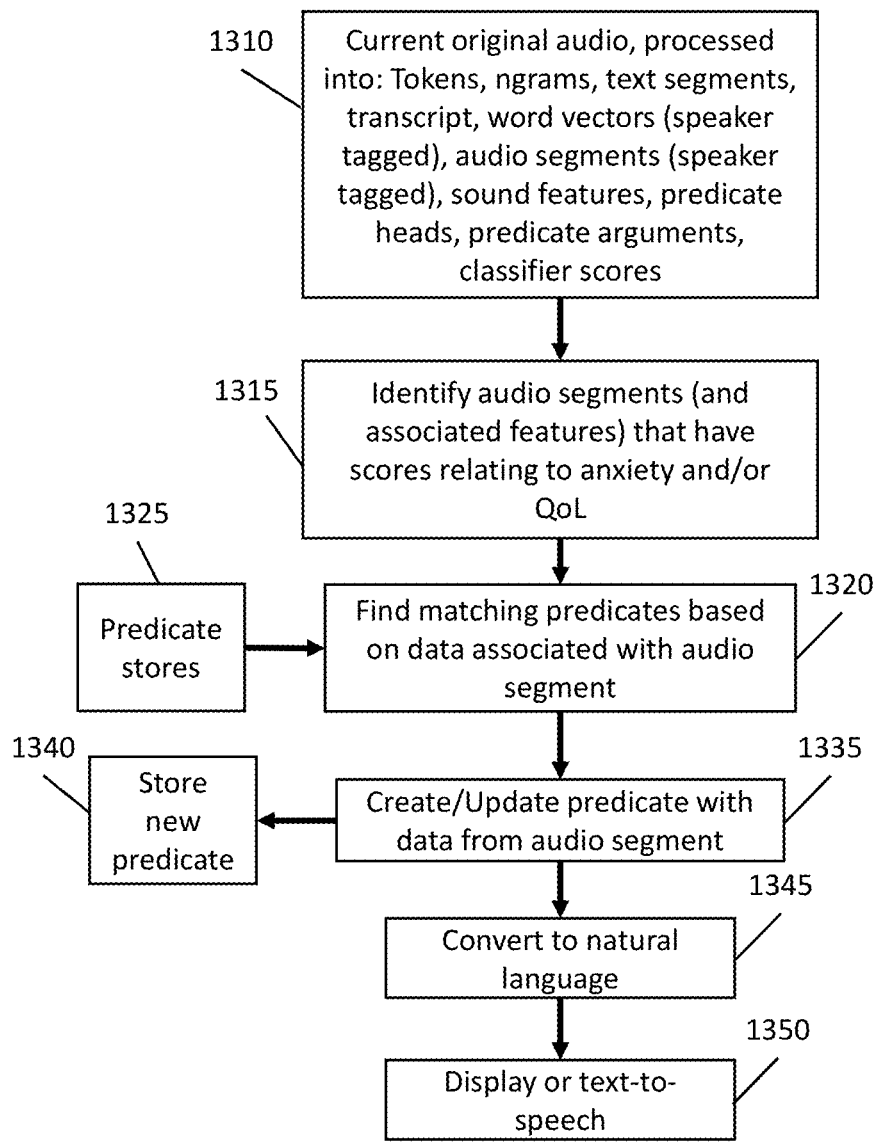
FIG. 13 is a flow diagram illustrating steps of an automated method for identifying an initial topic of interest in accordance with various embodiments of the present invention.

FIG. 13 corresponds to steps 305 and 310 of FIG. 3. Stated generally, an initial topic of interest for each audio segment is identified. This is the topic determined by the application of controller rules to topic candidates for each audio segment based on associated predicates. That initial topic of interest is then converted to natural language guidance calculated to suggest to the interviewer what to discuss with the subject that will address the subject's concern.

At block 1310, featurized data, as well classification scores, extractions, and predicate sets associated with the recent original audio input, are made available. The classification scores may also be translated into "labels," such as "high anxiety" and "low QoL" based on thresholds set by controller 105. In step 1315, "scored audio segments," which are audio segments that have associated health assessment classification scores, for example anxiety and/or QoL, are identified. In step 1320, the global and user predicate stores 1325 are searched for predicates based on data associated with the scored audio segments. This data may include the health assessment classifications scores, and/or the labels, and/or the featurized data, and/or predicates that have already been extracted for those audio segments from the original audio input. At step 1320, for each predicate identified from stores 1325, a predicate head is retrieved, (e.g., "bank account").

At step 1335, new predicates are created or updated by pairing the extracted predicate heads (e.g., "bank account") with data associates with the respective audio segment. The data may include the health assessment classifications scores, and/or the labels, and/or the featurized data. An example of Problog probabilistic programming for creating and updating this predicate is 0.85::high_anxiety(user12), 1.0::bank_account_balance(user12, $871)→0.8::anxiety_factor(user12, financial). This process is repeated for each pairing generated for an audio segment. The predicate store is updated at step 1340 with the newly created and updated predicate.

At step 1345, the system looks up a template stored in global predicate store 110 to identify a corresponding natural language semantic unit that serves as support for the interaction with the interviewer. Step 1345 converts the new predicate determined to be the initial topic of interest into as SVO, which then feeds into a language template for display purposes. At step 1350, the guidance is displayed, or otherwise communicated to the interviewer, for example by text-to-speech conversion.

Text-to-speech may use speech patterns and intonations derived from spectral analysis of participant's spoken words, reciprocity, and other voice data characteristics determined by use case developers to advance engagement in the interaction.

Figure 14:
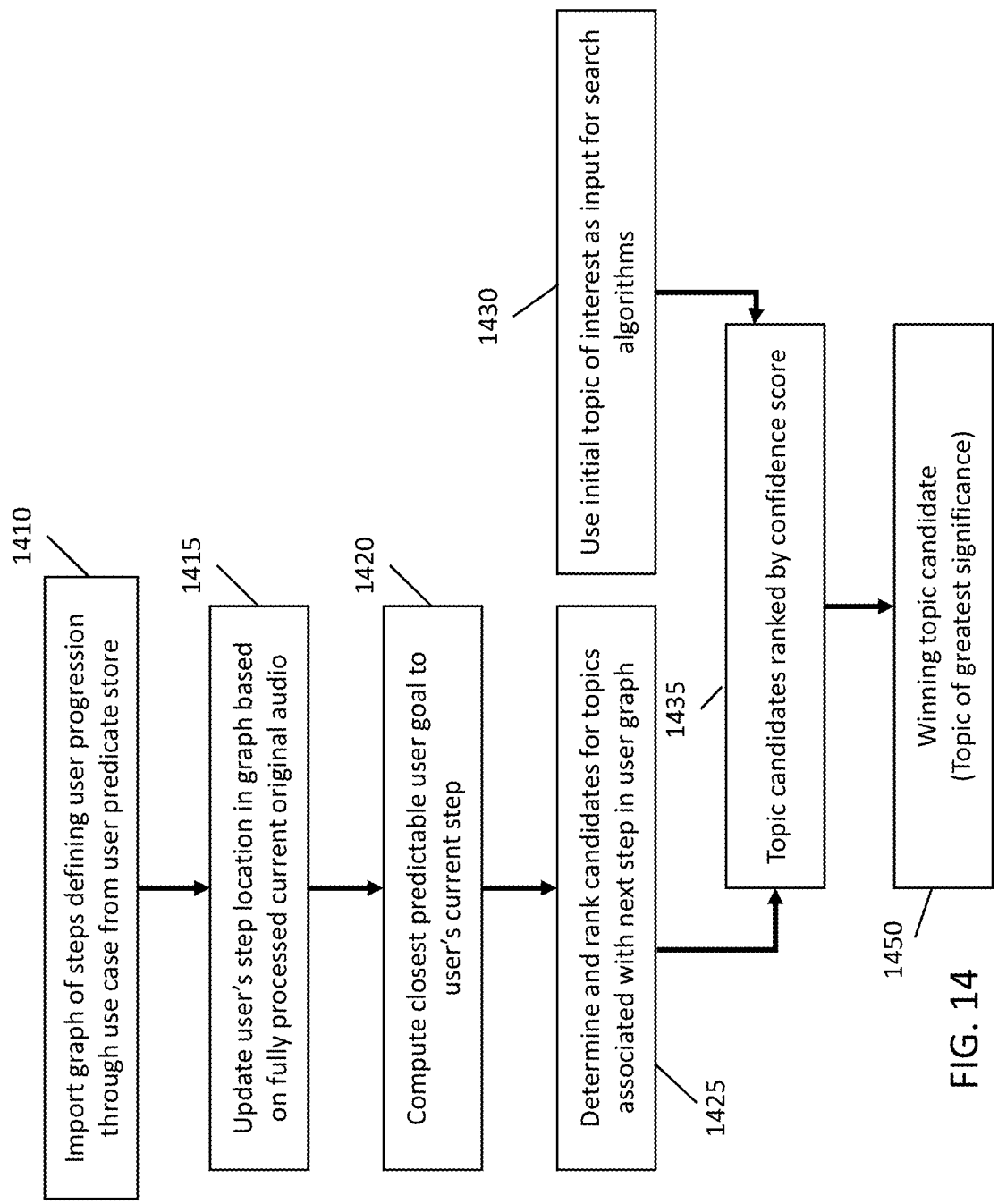
FIG. 14 is a flow diagram illustrating steps of an automated method for identifying a topic of greatest significance in accordance with various embodiments of the present invention.

FIG. 14 corresponds to step 315 of FIG. 3. As previously noted, the system determines not only what is of most interest as reflected by the recent conversation (the initial topic of interest), but taken with that, what topic/subject matter is most significant to the user's traversal of the use case overall. The functions illustrated in FIG. 14 accomplish this.

Specifically, using known methods, step 1410 derives from predicate stores 110 and 150 a graph representing each step along the overall use case path. One useful aspect of the predicate stores for mapping steps and a subject's location along a step path is that certain predicate sets represent goals. For example, predicate head, "weekly schedule," and predicate argument "Monday through Friday," represents a goal relevant to the earlier discussed use case, where the subject requires weekends free. Moreover, whether a goal is complete or incomplete can be inferred by checking whether the set of predicates on which it is dependent is completely satisfied. In this example if the predicate argument is "Monday through Friday," then the goal is complete. However, if the predicate argument remains "Thursday through Wednesday," then the goal is incomplete. Recognizing goals associated with the use case, and individual steps that must be completed to accomplish the goal, as complete or incomplete, contributes to developing the described graph and pinpointing the subject's location in the graph.

Accordingly, at step 1415, the graph is updated to reflect the subject's current location along that path. In step 1420, the closest predicable user goals to the user's current location in the graph is determined. For example, one nearby goal or step may be interviewing for a job that provides weekends free. At step 1425, the nearby steps are ranked according to rules set by controller 105 for the use case.

At step 1430, the initial topic of interest is provided. At step 1435, that topic is weighed with the topics identified at step 1425. At step 1435, the topics are ranked based on factors established by controller 105—defined use case rules including relevance, quality and actionability. At step 1450 a highest rank topic is selected as the topic of greatest significance. While the preferred embodiment uses extracted predicates and probabilistic programming to predict dynamically the topic of greatest significance to a user, conventional approaches to identifying user intent and mention extraction, typical of chatbot technologies, can be used as a default with a matrix linking extracted content and classifier scores to a pre-scripted response or set of actions. In such case, the live health classifier scores still work dynamically on extracted text using probability, even if the response or action is pre-scripted using an exact rather than probabilistic match.

Figure 15:
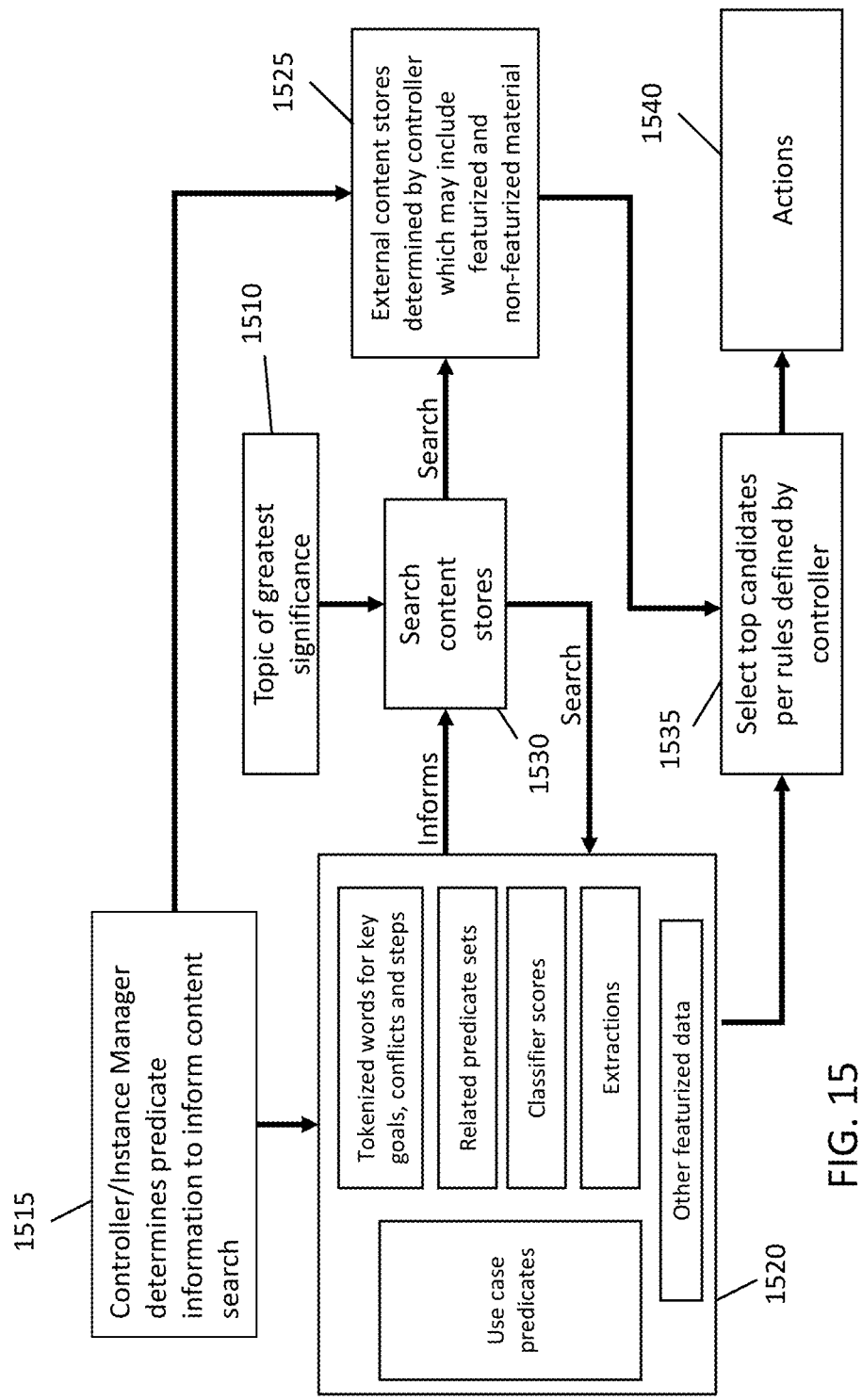
FIG. 15 is a flow diagram illustrating steps of an automated method for searching content in accordance with various embodiments of the present invention.

FIG. 15 corresponds to step 320 of FIG. 3, and steps 405, 410 and 415 of FIG. 4. Stated generally, the operation illustrated in FIG. 15 identifies content that is the basis for an action step or steps most closely associated with the identified topic of greatest significance. Specifically, the topic of greatest significance is provided at step 1510. At step 1515 controller 105 defines the scope of searchable content which resides both in the available use case predicate store 1520, and also among external content 1525.

As shown, the use case content in predicate store 1520, including goals and context reflected by that content, informs the search process 1530. At step 1530, based on the data provided from the use case content in predicate store 1520, and subject of greatest significance provided at block 1510, the content stores 1520 and 1525 are searched for content most closely correlated to the topic of greatest significance. At step 1535 candidates are ranked according to rules set by controller 105. One or more best next actions are then identified at step 1540.

The preferred method represented by FIG. 4 includes additional behavior in connection with the functions illustrated in FIG. 15. Specifically, for that preferred method, searchable content stores are confined to content that can relate only to an action step that i) has contact information available for the resource(s) that are required, ii) involves resources that can be marshalled immediately, and iii) involves a third party stakeholder who can also be contacting immediately, and who is in a position to supervise the execution of the action step.

Some portions of this description describe the embodiments of the invention in terms of algorithms. These operations, while described functionally, computationally, or logically, are understood to be implemented by computer programs or equivalent electrical circuits, micro-code, or the like. The described operations may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to herein may include a single processor or may be implemented with architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

The various embodiments can be further implemented in a wide variety of operating environments, which in some cases can include one or more user computers or computing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially available operating systems and other known applications for purposes such as database management. These devices can also include other electronic devices, such as dummy terminals, virtual terminals, thin-clients, and other devices capable of communicating via a network.

Embodiments can utilize at least one network that would be familiar to those skilled in the art for supporting communications using any of a variety of commercially available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network, or any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C # or C++ or any scripting language, such as Perl, Python, or TCL, as well as combinations thereof. The server(s) may also include database servers, including without limitation those commercially available from Oracle®, Microsoft®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element, or keypad) and at least one output device (e.g., a display screen, a display device, printer, or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed, and/or removable storage devices as well as storage media for temporarily and/or more permanently containing, storing, transmitting, and retrieving computer-readable information. The system and various devices also can include a number of software applications, modules, services, or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets, APIs, scripts, and the like), or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments and that many modifications and variations are possible.

The foregoing description of the embodiments of the invention has been presented for the purpose of illustration; it is not intended to be exhaustive or to limit the invention to the precise forms disclosed. The description and drawings are, accordingly, to be regarded in an illustrative rather than a restrictive sense. The language used in the specification has been principally selected for readability and instructional purposes. It is therefore intended that the scope of the invention be limited not by this detailed description and drawings, but rather by any claims that issue based on this application. It will, however, be evident that various modifications and changes may be made thereunto without departing from the broader spirit and scope of the invention as set forth in the claims.

What is claimed is:

1. A method for guiding a support interaction between a human user and a human interviewer in real time, comprising the steps of:
  receiving an audio content from the user;
  generating from said audio content featurized audio data comprising a plurality of audio segments and a plurality of audio features using at least one language featurization system trained on a reference speech data;
  generating from said featurized audio data a classification score corresponding to at least one of said plurality of audio segments;
  displaying, in real time, said classification score and a transcribed text portion corresponding to said at least one of said plurality of audio segments;
  updating with a user predicate extracted from said at least one of said plurality of audio segments, a user database comprising user predicates;
  identifying an initial topic of interest to the user based upon said classification score, said at least one of said plurality of audio segments, said user predicate in said user database, and a use case predicate in a global database comprising use case predicates;
  converting said initial topic of interest to a natural language support interaction guidance for the interviewer;
  displaying said natural language support interaction guidance for the interviewer to the interviewer in real time;
  identifying a topic of greatest significance to the user based upon said initial topic of interest to the user, said classification score, at least one user predicate in said user database, and at least one use case predicate in said global database;
  identifying a highest correlated action step based upon said topic of greatest significance to the user; and
  communicating, to the interviewer, said highest correlated action step.

2. The method of claim 1, wherein said plurality of audio features comprise sound features comprising loudness characteristics, power characteristics, and pitch characteristics.

3. The method of claim 1, wherein said reference speech data comprises audio from clinical trial data previously measured on clinically recognized health instruments.

4. The method of claim 3, wherein said clinically recognized health instruments comprise a General Anxiety Disorder evaluation.

5. The method of claim 1, wherein said classification score comprises at least one of an anxiety measure and a quality of life measure.

6. The method of claim 1, wherein the step of generating comprises the step of generating classification scores with a classifier trained on said reference speech data.

7. The method of claim 1, further comprising the step of extracting said user predicate from said at least one of said plurality of audio segments with an extractor trained on said reference speech data.

8. The method of claim 1, wherein said user database further comprises a plurality of classification scores.

9. The method of claim 1, wherein the step of communicating comprises displaying in real time to the interviewer said highest correlated action step.

10. The method of claim 1, wherein the step of identifying a topic of greatest significance comprises the steps of:
  determining a user status in a use case, based on matching said initial topic of interest and a health assessment score to a stored use case predicate;
  predicting a user goal based upon said user status and said use case;
  determining, from a plurality of topics associated with said user goal, a highest ranked topic;
  identifying, based on said highest ranked topic and a plurality of use case action steps in said use case, a next action step; and
  implementing said next action step.

11. The method of claim 10, wherein the step of implementing comprises communicating said next action step.

12. The method of claim 11, wherein the step of communicating comprises the step of contacting a third person different from the human user and the human interviewer.

13. The method of claim 10, wherein the step of determining, from a plurality of topics associated with said user goal, a highest ranked topic comprises the step of ranking said plurality of topics based on a respective confidence level for each topic.

14. The method of claim 10, wherein the step of determining, from a plurality of topics associated with said user goal, a highest ranked topic comprises the step of ranking said plurality of topics based on a respective relevance level for each topic.

15. The method of claim 10, wherein the step of determining, from a plurality of topics associated with said user goal, a highest ranked topic comprises the step of ranking said plurality of topics based on a respective actionability level for each topic.

16. A method for guiding a support interaction between a human user and a human interviewer in real time, comprising the steps of:
  receiving an audio content from the user;
  generating in real time from said audio content a featurized audio data comprising a plurality of audio segments and a plurality of audio features, using at least one language featurization system trained on a featurized reference speech data;
  wherein said featurized reference speech data comprises word vectors and sound features;
  generating, using a health assessment classification system trained on said featurized reference speech data, in real time from said featurized audio data a health assessment score for the user corresponding to at least one of said plurality of audio segments; and
  communicating in real time to the interviewer said health assessment score and a transcribed text portion corresponding to said at least one of said plurality of audio segments.

17. The method of claim 16, wherein said plurality of audio features comprise sound features comprising loudness characteristics, power characteristics, and pitch characteristics.

18. The method of claim 16, wherein said featurized reference speech data comprises featurized audio and featurized text, both from clinical trial data previously measured on clinically recognized health instruments.

19. The method of claim 16, further comprising the steps of:
  identifying in real time an initial topic of interest to the user based upon said health assessment score and said at least one of said plurality of audio segments; and wherein the step of communicating further comprises communicating to the interviewer in real time said initial topic of interest.

20. The method of claim 19, wherein the step of communicating comprises displaying in real time to the interviewer said health assessment score, said transcribed text portion, and said initial topic of interest.

21. A method for guiding a support interaction between a human user and a human interviewer in real time, comprising the steps of:
   receiving an audio content from the user;
   generating from said audio content featurized audio data comprising a plurality of audio segments and a plurality of audio features using at least one language featurization system trained on a reference speech data;
   generating in real time from said featurized audio data a classification and a classification level, within a range of classification levels above a classification threshold level, corresponding to at least one of said plurality of audio segments;
   determining, from said classification and said classification level, a General Anxiety Disorder score for the user;
   displaying in real time to the interviewer said General Anxiety Disorder score and a transcribed text portion corresponding to said at least one of said plurality of audio segments;
   updating with a user predicate extracted from said at least one of said plurality of audio segments, a user database comprising user predicates;
   identifying an initial topic of interest to the user based upon said General Anxiety Disorder score, said at least one of said plurality of audio segments, said user predicate in said user database, and a use case predicate in a global database comprising use case predicates;
   converting said initial topic of interest to a natural language support interaction guidance for the interviewer; and
   displaying said natural language support interaction guidance for the interviewer to the interviewer in real time.

22. The method of claim 21, further comprising the steps of:
   identifying a topic of greatest significance to the user based upon said General Anxiety Disorder score, said initial topic of interest, at least one user predicate in said user database, and at least one use case predicate in said global database; and
   identifying a highest correlated action step based upon said topic of greatest significance to the user; and
   communicating to the interviewer said highest correlated action step.

23. The method of claim 22, wherein the step of identifying a topic of greatest significance comprises the steps of:
   determining a user status in a use case, based on matching said initial topic of interest and a health assessment score to a stored use case predicate;
   predicting a user goal based upon said user status and said use case;
   determining, from a plurality of topics associated with said user goal, a highest ranked topic;
   identifying, based on said highest ranked topic and a plurality of use case action steps in said use case, a next action step; and
   implementing said next action step.

24. The method of claim 23, wherein the step of implementing comprises communicating said next action step.

25. The method of claim 24, wherein the step of communicating comprises the step of contacting a third person different from the human user and the human interviewer.

26. The method of claim 23, wherein the step of determining, from a plurality of topics associated with said user goal, a highest ranked topic comprises the step of ranking said plurality of topics based on a respective confidence level for each topic.

27. The method of claim 23, wherein the step of determining, from a plurality of topics associated with said user goal, a highest ranked topic comprises the step of ranking said plurality of topics based on a respective relevance level for each topic.

28. The method of claim 23, wherein the step of determining, from a plurality of topics associated with said user goal, a highest ranked topic comprises the step of ranking said plurality of topics based on a respective actionability level for each topic.

29. The method of claim 21, wherein said classification comprises an anxiety measure and wherein said classification level comprises a high anxiety level.

30. The method of claim 21, further comprising the step of identifying a plurality of predicates associated with certain ones of said plurality of audio segments with an extractor trained on said reference speech data.

31. The method of claim 21, wherein said plurality of audio features comprise sound features comprising loudness characteristics, power characteristics, and pitch characteristics.

32. The method of claim 21, wherein said reference speech data comprises audio and text, both from clinical trial data previously measured on clinically recognized health instruments.

33. A method for guiding a support interaction between a human user and a human interviewer in real time, comprising the steps of:
   receiving an audio content from the user;
   generating from said audio content featurized audio data comprising a plurality of audio segments and a plurality of audio features using at least one language featurization system trained on a reference speech data;
   generating in real time from said featurized audio data a classification and a classification level, within a range of classification levels above a classification threshold level, corresponding to at least one of said plurality of audio segments;
   determining, from said classification and said classification level, a quality of life score for the user;
   displaying in real time to the interviewer said quality of life score for the user and a transcribed text portion corresponding to said at least one of said plurality of audio segments;
   updating with a user predicate extracted from said at least one of said plurality of audio segments, a user database comprising user predicates;
   identifying an initial topic of interest to the user based upon said quality of life score, said at least one of said plurality of audio segments, said user predicate in said user database, and a use case predicate in a global database comprising use case predicates;
   converting said initial topic of interest to a natural language support interaction guidance for the interviewer; and
   displaying said natural language support interaction guidance for the interviewer to the interviewer in real time.

34. The method of claim 33, further comprising the steps of:
- identifying a topic of greatest significance to the user based upon said quality of life score, said initial topic of interest, at least one user predicate in said user database, and at least one use case predicate in said global database; and
- identifying a highest correlated action step based upon said topic of greatest significance; and
- communicating to the interviewer said highest correlated action step.

35. The method of claim 34, wherein the step of identifying a topic of greatest significance comprises the steps of:
- determining a user status in a use case, based on matching said initial topic of interest and a health assessment score to a stored use case predicate;
- predicting a user goal based upon said user status and said use case;
- determining, from a plurality of topics associated with said user goal, a highest ranked topic;
- identifying, based on said highest ranked topic and a plurality of use case action steps in said use case, a next action step; and
- implementing said next action step.

36. The method of claim 35, wherein the step of implementing comprises communicating said next action step.

37. The method of claim 36, wherein the step of communicating comprises the step of contacting a third person different from the human user and the human interviewer.

38. The method of claim 35, wherein the step of determining, from a plurality of topics associated with said user goal, a highest ranked topic comprises the step of ranking said plurality of topics based on a respective confidence level for each topic.

39. The method of claim 35, wherein the step of determining, from a plurality of topics associated with said user goal, a highest ranked topic comprises the step of ranking said plurality of topics based on a respective relevance level for each topic.

40. The method of claim 35, wherein the step of determining, from a plurality of topics associated with said user goal, a highest ranked topic comprises the step of ranking said plurality of topics based on a respective actionability level for each topic.

41. The method of claim 33, wherein said plurality of audio features comprise sound features comprising loudness characteristics, power characteristics, and pitch characteristics.

42. The method of claim 33, wherein said reference speech data comprises audio from clinical trial data previously measured on clinically recognized health instruments.

43. The method of claim 33, wherein said classification comprises a quality of life measure and wherein said classification level comprises a high quality of life level.

44. The method of claim 33, further comprising the step of identifying a plurality of predicates associated with certain ones of said plurality of audio segments with an extractor trained on said reference speech data.

45. A method for guiding a support interaction between a human user and a human interviewer in real time, comprising the steps of:
- receiving an audio content from the user;
- generating in real time from said audio content a featurized audio data comprising a plurality of audio segments and a plurality of audio features, using at least one language featurization system trained on a featurized reference speech data;
- generating, using a health assessment classification system trained on said featurized reference speech data, in real time from said featurized audio data, a health assessment score corresponding to at least one of said plurality of audio segments;
- updating with a user predicate extracted from said at least one of said plurality of audio segments, a user database comprising user predicates;
- identifying an initial topic of interest to the user based upon said health assessment score, said at least one of said plurality of audio segments, said user predicate in said user database; and a use case predicate in a global database comprising use case predicates;
- determining a user status in a use case, based on matching said initial topic of interest and said health assessment score to a stored use case predicate;
- predicting a user goal based upon said user status and said use case;
- determining, from a plurality of topics associated with said user goal, a highest ranked topic;
- identifying, based on said highest ranked topic and a plurality of use case action steps in said use case, a next action step; and
- implementing said next action step.

46. The method of claim 45, wherein the step of implementing comprises communicating said next action step.

47. The method of claim 46, wherein the step of communicating comprises the step of contacting a third person different from the human user and the human interviewer.

48. The method of claim 45, wherein the step of determining, from a plurality of topics associated with said user goal, a highest ranked topic comprises the step of ranking said plurality of topics based on a respective confidence level for each topic.

49. The method of claim 45, wherein the step of determining, from a plurality of topics associated with said user goal, a highest ranked topic comprises the step of ranking said plurality of topics based on a respective relevance level for each topic.

50. The method of claim 45, wherein the step of determining, from a plurality of topics associated with said user goal, a highest ranked topic comprises the step of ranking said plurality of topics based on a respective actionability level for each topic.

51. A method for guiding a support interaction between a human user and a human interviewer in real time, comprising the steps of:
- receiving an audio content from the user;
- generating in real time from said audio content a featurized audio data comprising a plurality of audio segments and a plurality of audio features, using at least one language featurization system trained on a featurized reference speech data;
- wherein said featurized reference speech data comprises word vectors and sound features;
- generating, using a health assessment classification system trained on said featurized reference speech data, in real time from said featurized audio data a health assessment score for the user corresponding to at least one of said plurality of audio segments;
- identifying in real time at least one initial topic of interest to the user based upon said health assessment score and said at least one of said plurality of audio segments; and
- communicating in real time to the interviewer said health assessment score and said at least one initial topic of interest.

52. The method of claim 51, wherein the step of communicating comprises displaying in real time to the interviewer said health assessment score and said at least one initial topic of interest.

\* \* \* \* \*